US012605083B2

(12) United States Patent
Houck

(10) Patent No.: US 12,605,083 B2
(45) Date of Patent: Apr. 21, 2026

(54) OPTICAL SENSOR DEVICE

(71) Applicant: VIAVI Solutions Inc., San Jose, CA (US)

(72) Inventor: William D. Houck, Santa Rosa, CA (US)

(73) Assignee: VIAVI Solutions Inc., Chandler, AZ (US)

( * ) Notice: Subject to any disclaimer, the term of this patent is extended or adjusted under 35 U.S.C. 154(b) by 1038 days.

(21) Appl. No.: 17/228,139

(22) Filed: Apr. 12, 2021

(65) Prior Publication Data

US 2021/0338090 A1 Nov. 4, 2021

Related U.S. Application Data

(60) Provisional application No. 63/018,940, filed on May 1, 2020.

(51) Int. Cl.
*A61B 5/026* (2006.01)
*A61B 5/0215* (2006.01)
*A61B 5/1455* (2006.01)

(52) U.S. Cl.
CPC ........ *A61B 5/0261* (2013.01); *A61B 5/02154* (2013.01); *A61B 5/14551* (2013.01)

(58) Field of Classification Search
CPC .............. A61B 5/0261; A61B 5/02154; A61B 5/14551; A61B 5/1455; A61B 5/01;
(Continued)

(56) References Cited

U.S. PATENT DOCUMENTS 4,141,036 A * 2/1979 Diehl ..................... H04N 23/84
348/277
5,981,951 A * 11/1999 Essen-Moller .... A61B 5/14532
250/341.1
(Continued)

FOREIGN PATENT DOCUMENTS

CN 105637332 A 6/2016
CN 106256313 A 12/2016
(Continued)

OTHER PUBLICATIONS

Extended European Search Report for Application No. EP21171376.3, mailed on Sep. 29, 2021, 7 pages.
(Continued)

*Primary Examiner* — David Hamaoui
*Assistant Examiner* — Rumaisa Rashid Baig
(74) *Attorney, Agent, or Firm* — FOLEY & LARDNER LLP

(57) ABSTRACT

An optical channel, of an optical filter, passes light associated with a particular wavelength range to a sensor element, of an optical sensor, that operates in a gated mode. One or more processors obtain, from the optical sensor, a first optical measurement and a second optical measurement related to a multi-layered subject. The first optical measurement indicates an amount of light associated with the particular wavelength range that the sensor element accumulated during a first time range, and the second optical measurement indicates an amount of light associated with the particular wavelength range that the sensor element accumulated during a second time range. The first time range is a subrange of the second time range. The one or more processors process the first optical measurement and the second optical measurement to determine one or more parameters associated with the multi-layered subject.

20 Claims, 17 Drawing Sheets

(58) Field of Classification Search

CPC ............ A61B 5/02007; A61B 5/02028; A61B 5/02055; A61B 5/14532; A61B 5/4872; G01J 3/0256; G01J 3/0291; G01J 2003/1213; G01J 3/2803; G01J 3/2889; G01J 3/0205; G01J 1/0407; G01J 3/2823; G01J 2003/2826

See application file for complete search history.

(56) References Cited

U.S. PATENT DOCUMENTS

| | | | |
|---|---|---|---|
| 6,097,021 A | | 8/2000 | Aswell et al. |
| 8,072,595 B1* | | 12/2011 | Bastiaans ........... G01N 21/7703 |
| | | | 356/301 |
| 8,694,067 B2* | | 4/2014 | Huiku ............... A61B 5/14551 |
| | | | 600/323 |
| 9,933,298 B2 | | 4/2018 | Likovich et al. |
| 10,104,315 B2 | | 10/2018 | Ando et al. |
| 10,165,955 B2* | | 1/2019 | Gladshtein ........... A61B 3/1241 |
| 10,231,634 B2* | | 3/2019 | Zand .................. A61B 5/14542 |
| 10,366,269 B2 | | 7/2019 | Lu et al. |
| 10,587,090 B1* | | 3/2020 | Raring ............... H01S 5/32341 |
| 10,660,531 B1* | | 5/2020 | Libove .................. A61B 5/369 |
| 10,687,717 B1* | | 6/2020 | Peterson ........... A61B 5/14551 |
| 11,489,543 B1* | | 11/2022 | Parthasarathy ..... H03M 7/3062 |
| 2004/0179774 A1* | | 9/2004 | Delpiano ............. H01S 5/0687 |
| | | | 385/24 |
| 2005/0259254 A1* | | 11/2005 | Soller ....................... G01J 3/10 |
| | | | 315/307 |
| 2006/0253007 A1 | | 11/2006 | Cheng et al. |
| 2009/0216097 A1* | | 8/2009 | Wilson ................ A61B 5/1459 |
| | | | 600/327 |
| 2009/0238557 A1* | | 9/2009 | Chen .................... H01S 5/0687 |
| | | | 398/16 |
| 2011/0082355 A1* | | 4/2011 | Eisen .................. A61B 5/7207 |
| | | | 600/324 |
| 2011/0174987 A1* | | 7/2011 | Sawada .................. G01J 3/027 |
| | | | 250/214 R |
| 2011/0213217 A1* | | 9/2011 | McKenna .......... A61B 5/14552 |
| | | | 600/301 |
| 2012/0113160 A1* | | 5/2012 | Kurokawa .............. G06F 3/042 |
| | | | 362/84 |
| 2012/0136225 A1* | | 5/2012 | Benni .................. A61B 5/7271 |
| | | | 600/323 |
| 2012/0278043 A1* | | 11/2012 | Lewis .................... G01H 9/004 |
| | | | 702/189 |
| 2013/0079647 A1* | | 3/2013 | McGonigle .......... A61B 5/7239 |
| | | | 600/300 |
| 2013/0155410 A1* | | 6/2013 | Enderby ............ A61B 5/14532 |
| | | | 356/445 |
| 2013/0258093 A1* | | 10/2013 | Jingu ................. G01N 21/9501 |
| | | | 348/92 |
| 2014/0233039 A1* | | 8/2014 | Takahashi ............ G01N 21/253 |
| | | | 356/519 |
| 2015/0190063 A1* | | 7/2015 | Zakharov ............. A61B 5/1107 |
| | | | 600/479 |
| 2016/0216376 A1* | | 7/2016 | Patil ........................ G01S 17/36 |
| 2016/0242682 A1 | | 8/2016 | Gulati et al. |
| 2016/0344965 A1* | | 11/2016 | Grauer ................. H04N 25/587 |
| 2016/0373652 A1* | | 12/2016 | Ando ................... A61B 5/4064 |
| 2017/0051884 A1* | | 2/2017 | Raring ................... H01S 5/22 |
| 2017/0188959 A1* | | 7/2017 | Banet .................. A61B 5/7282 |
| 2017/0237891 A1* | | 8/2017 | De Coi .................. H04N 5/265 |
| | | | 348/231.99 |
| 2017/0303861 A1* | | 10/2017 | Bechtel ............. A61B 5/14552 |
| 2017/0332029 A1* | | 11/2017 | Feick .................... G01S 7/4914 |
| 2017/0336271 A1* | | 11/2017 | Contreras ................ G01K 7/16 |
| 2018/0070886 A1* | | 3/2018 | Fairchild .................. A61B 5/48 |
| 2018/0146866 A1 | | 5/2018 | Chachisvilis et al. |
| 2018/0214057 A1* | | 8/2018 | Schultz ................. G01J 1/0407 |
| 2018/0303391 A1* | | 10/2018 | Roblyer .............. A61B 5/0075 |
| 2018/0313692 A1 | | 11/2018 | Yang et al. |
| 2018/0333060 A1* | | 11/2018 | Mazzillo ............ A61B 5/02433 |
| 2019/0028660 A1* | | 1/2019 | Ando .................... H04N 25/63 |
| 2019/0033135 A1 | | 1/2019 | Haider et al. |
| 2019/0134308 A1* | | 5/2019 | Newberry ......... A61M 5/14248 |
| 2019/0273876 A1* | | 9/2019 | Ando .................... H04N 23/11 |
| 2019/0282125 A1* | | 9/2019 | Durnin .............. A61B 5/02416 |
| 2019/0323663 A1* | | 10/2019 | Rudy .................. H01S 5/34333 |
| 2019/0370447 A1* | | 12/2019 | Houck .................. G02B 5/285 |
| 2020/0064861 A1* | | 2/2020 | Zhang .................... G01S 19/13 |
| 2020/0297270 A1* | | 9/2020 | Ando .................... A61B 5/363 |
| 2020/0309911 A1* | | 10/2020 | Meissner ............. G01S 7/4861 |
| 2020/0364445 A1* | | 11/2020 | Suzuki ............... G06V 10/145 |
| 2020/0375476 A1* | | 12/2020 | Franceschini ........ A61B 5/0261 |
| 2021/0055473 A1* | | 2/2021 | Shnaiderman ........ G01L 11/025 |
| 2021/0075978 A1* | | 3/2021 | Sowa ................... H04N 25/11 |
| 2021/0120193 A1* | | 4/2021 | Swager .................... G01J 5/02 |
| 2021/0196109 A1* | | 7/2021 | Shelton, IV .......... A61B 90/30 |
| 2021/0199557 A1* | | 7/2021 | Shelton, IV ......... G01B 11/026 |
| 2021/0236006 A1* | | 8/2021 | Nakamura ............. A61B 5/165 |
| 2022/0299646 A1* | | 9/2022 | Hsieh ................ H01L 27/14636 |
| 2022/0373392 A1* | | 11/2022 | Kurki ...................... G01J 3/44 |
| 2023/0068923 A1* | | 3/2023 | Yamakoshi ............ H04N 23/13 |
| 2023/0346231 A1* | | 11/2023 | Mcgrath ........... A61B 5/02416 |

FOREIGN PATENT DOCUMENTS

| | | |
|---|---|---|
| CN | 109069001 A | 12/2018 |
| KR | 10-2018-0117120 A | 10/2018 |
| KR | 10-2019-0012062 A | 2/2019 |
| WO | 2019124023 A1 | 6/2019 |
| WO | 2019170716 A1 | 9/2019 |

OTHER PUBLICATIONS

Y. Shirakawa, et al.; "An 8-Tap CMOS Lock-In Pixel Image Sensor for Short-Pulse Time-of-Flight Measurements"; Sensors; Feb. 4, 2020; 16 pages; MDPI.

* cited by examiner

146

Determine a first depth range
of the subject 104

148

Process the first optical
measurement to determine one
or more first characteristics
associated with the first depth
range of the subject 104

144

First optical
measurement at
time T₁

152
Determine a second depth range of the subject 104

154
Process the first optical measurement and the second optical measurement to determine one or more second characteristics associated with the second depth range of the subject 104

156
Determine one or more parameters associated with the subject 104

150
Second optical measurement at time T₂

500

710 Obtain, from the optical sensor, a first optical measurement and a second optical measurement related to a subject 720 Process the first optical measurement and the second optical measurement to determine one or more parameters associated with the subject 730 Provide information indicating the one or more parameters associated with the subject

700

OPTICAL SENSOR DEVICE

RELATED APPLICATION

This application claims priority to U.S. Provisional Patent Application No. 63/018,940, filed on May 1, 2020, and entitled "OPTICAL TISSUE MODELING," the content of which is incorporated by reference herein in its entirety.

BACKGROUND

An optical sensor device may be utilized to capture information concerning light. For example, the optical sensor device may capture information relating to a set of wavelengths associated with the light. The optical sensor device may include a set of sensor elements (e.g., optical sensors, spectral sensors, and/or image sensors) that capture the information. For example, an array of sensor elements may be utilized to capture information relating to multiple wavelengths. The sensor element array may be associated with an optical filter. The optical filter may include one or more channels that respectively pass particular wavelengths to sensor elements of the sensor element array.

SUMMARY

In some implementations, an optical sensor device includes an optical sensor comprising an array of sensor elements, wherein a sensor element, of the array of sensor elements, is configured to operate in a gated mode; wherein an optical channel, of the array of optical channels, is disposed over the sensor element and is configured to pass light associated with a particular wavelength range to the sensor element; and one or more processors configured to: obtain, from the optical sensor, a first optical measurement and a second optical measurement related to a multi-layered subject, wherein the first optical measurement indicates an amount of light associated with the particular wavelength range that the sensor element accumulated during a first time range, and wherein the second optical measurement indicates an amount of light associated with the particular wavelength range that the sensor element accumulated during a second time range, wherein the first time range is a subrange of the second time range; process the first optical measurement and the second optical measurement to determine one or more parameters associated with the multi-layered subject; and provide information indicating the one or more parameters associated with the multi-layered subject.

In some implementations, an optical sensor device includes an optical sensor comprising an array of sensor elements; and one or more processors, wherein: a first sensor element, of the array of sensor elements, is configured to: provide, based on a transfer cycle and to the one or more processors, a first optical measurement associated with a subject that indicates an amount of light associated with a first wavelength range that the first sensor element accumulated during a first time range, and provide, based on the transfer cycle and to the one or more processors, a second optical measurement associated with the subject that indicates an amount of light associated with the first wavelength range that the first sensor element accumulated during a second time range, wherein a period of the transfer cycle is less than 10 nanoseconds; a second sensor element, of the array of sensor elements, is configured to: provide, based on a transfer cycle and to the one or more processors, a third optical measurement associated with the subject that indicates an amount of light associated with a second wavelength range that the second sensor element accumulated during the first time range, and provide, based on the transfer cycle and to the one or more processors, a fourth optical measurement associated with the subject that indicates an amount of light associated with the second wavelength range that the second sensor element accumulated during the second time range; and the one or more processors are configured to: process the first optical measurement, the second optical measurement, the third optical measurement, and the fourth optical measurement to determine one or more parameters associated with the subject, and provide information indicating the one or more parameters associated with the subject.

In some implementations, a method includes obtaining, by an optical sensor device and from an optical sensor of the optical sensor device, a first optical measurement and a second optical measurement related to a mammalian body part, wherein the first optical measurement indicates an amount of light associated with a particular wavelength range that a sensor element of the optical sensor accumulated during a first time range, and wherein the second optical measurement indicates an amount of light associated with the particular wavelength range that the sensor element accumulated during a second time range, wherein the first time range is a subrange of the second time range; processing, by the optical sensor device, the first optical measurement and the second optical measurement to determine one or more health parameters associated with the mammalian body part; and providing, by the optical sensor device, information indicating the one or more parameters associated with the mammalian body part.

DETAILED DESCRIPTION

Figure 1A:
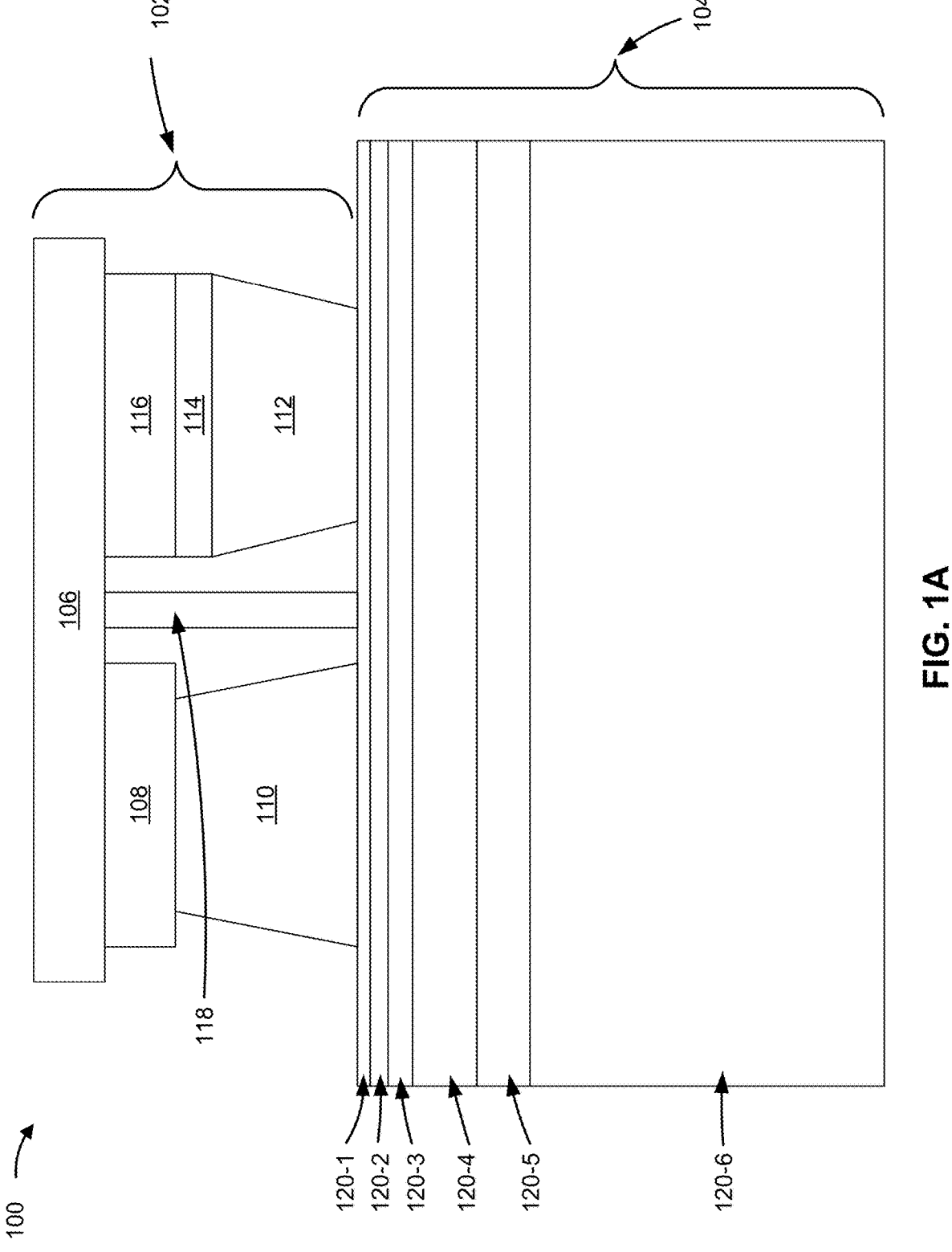
FIGS. 1A-1E are diagrams of an example implementation described herein.

The following detailed description of example implementations refers to the accompanying drawings. The same reference numbers in different drawings may identify the same or similar elements. The following description uses a spectrometer as an example. However, the techniques, principles, procedures, and methods described herein may be used with any sensor, including but not limited to other optical sensors and spectral sensors.

An optical sensor device may be used to determine an optical measurement associated with a subject. In some cases, the optical sensor device may determine one or more optical measurements related to light that has propagated through the subject and may determine one or more parameters associated with the subject based on the optical measurement. For example, when the subject is human body tissue, the optical sensor device may determine one or more optical measurements related to light that has propagated through the human body tissue to determine a health parameter related to the human body tissue, such as a blood oxygen parameter of the human body tissue. However, the subject may comprise different spectral properties at different depth ranges (e.g., the subject may comprise multiple layers that have different respective spectral properties) and therefore the one or more optical measurements determined by the optical sensor device may include information associated with one or more depth ranges that are not relevant to determining a parameter associated with the subject. This can lead to a lower signal to noise ratio associated with the one or more optical measurements, which affects an ability of the optical sensor device to accurately determine the one or more parameters of the subject.

Some implementations described herein provide an optical sensor device that includes an optical sensor comprising an array of sensor elements and one or more processors. A sensor element, of the array of sensor elements, may be configured to operate in a gated mode. For example, the sensor element may include components to capture light associated with a particular wavelength range (e.g., that is emitted by a light source of the optical sensor device and has propagated through one or more layers of a multi-layered subject), accumulate a charge associated with the photocurrent, and convert the accumulated charge to an optical measurement. The components may be configured to convert the accumulated charge to the optical measurement based on a transfer cycle, which may have a period that is less than 10 nanoseconds. Accordingly, the sensor element may be configured to provide an optical measurement at a high frequency (e.g., at time intervals of less than 10 nanoseconds), which is not possible with conventional sensor elements that are required to be reset between measurement cycles.

The one or more processors may be configured to obtain optical measurements from the optical sensor. For example, the one or more processors may obtain a first optical measurement that indicates an amount of light associated with the particular wavelength range that the sensor element accumulated during a first time range and a second optical measurement that indicates an amount of light associated with the particular wavelength range that the sensor element accumulated during a second time range. Because the optical measurements are related to an accumulated charge of the sensor element, the first time range may be a subrange of the second time range. Accordingly, the one or more processors may process the first optical measurement to determine one or more first characteristics associated with a first depth range (e.g., a first layer) of the subject and may process the first optical measurement and the second optical measurement (e.g., by processing a difference between the first optical measurement and the second optical measurement) to determine one or more second characteristics associated with a second depth range (e.g., a second layer) of the subject.

In this way, because the optical sensor is able to provide optical measurements at a high frequency (e.g., at time intervals of less than 10 nanoseconds), the one or more processors may determine, based on the optical measurements, respective characteristics of individual layers of a subject rather than characteristics of multiple layers of the subject. This allows the one or more processors to process the respective characteristics of the individual layers to improve a likelihood of accurately determining one or more parameters associated with the subject. For example, when the subject is multi-layered tissue of a mammalian body part, such as multi-layered tissue of a human body part, the one or more processors may ignore characteristics associated with one or more upper layers of the subject (e.g., one or more dermis layers) and may process characteristics associated with a lower layer (e.g., a subcutaneous tissue layer) to determine one or more deep-tissue health parameters, such as a body fat composition parameter. As another example, the one or more processors may compare characteristics associated with one or more layers of the subject (e.g., one or more dermis layers) to determine one or more blood level health parameters, such as a blood glucose level parameter, a blood pressure parameter, or a blood oxygen parameter.

FIGS. 1A-1E are diagrams of an overview of an example implementation 100 described herein. As shown in FIG. 1A, example implementation 100 may include an optical sensor device 102 and a subject 104. The optical sensor device 102 may be configured to obtain optical measurements related to the subject 104 and to determine, based on the optical measurements, one or more parameters associated with the subject 104, as described herein.

As further shown in FIG. 1A, the optical sensor device 102 may include one or more components, such as a printed circuit board (PCB) 106, a light source 108, an emission optic 110, a collection optic 112, an optical filter 114, an optical sensor 116, and/or a barrier 118.

The light source 108 and the optical sensor 116 may be attached and/or mounted to the PCB 106. The light source 108 may include one or more devices capable of generating light. For example, the light source 108 may include one or more light emitting diodes (LED), such as one or more phosphor LEDs. The light source 108 may be configured to provide light in a particular range (e.g., associated with visible light, infrared light, and/or ultraviolet light, among other examples). For example, an LED may provide light in a range of 700 nanometers to 1100 nanometers, which may enable sensing (e.g., by the optical sensor 116) based on light in the near-infrared (NIR) range. As another example, the light source 108 may be configured to provide light in a broad range. For example, one or more LEDs may provide light in a range of 300 nanometers to 2000 nanometers, which may enable sensing (e.g., by the optical sensor 116) based on broad spectrum light.

In some implementations, the light source 108 may include a single modulated LED or a plurality of modulated LEDs. When the light source 104 includes one or more modulated LEDs, the optical sensor device 102 (e.g., using the PCB 106) may modulate a power supply of the light source 108. Using a modulated LED may enable driving the LED to a higher power than a power of a continuous-wave LED. Furthermore, modulation may improve signal to noise properties of sensing performed using light from the modulated LED.

The light generated by the light source 108 may emit toward the emission optic 110. The emission optic 110 may include a lens, a window, an optical diffuser, an optical filter, an aperture stop, a reflective optical element, a diffractive optical element, a refractive optical element, and/or the like. In some implementations, the emission optic 110 may be configured to receive and to direct light emitted by the light source 108 toward the subject 104. The emission optic 110 may be proximate to the subject 104 (e.g., close to the subject 104) to allow the light to transmit from the emission optic 110 into the subject 104.

As further shown in FIG. 1A, the subject 104 may comprise one or more layers 120 (shown in FIG. 1A as layers 120-1 through 120-6). In some implementations, the subject 104 may comprise multi-layered tissue of a mammalian body part, such as multi-layered tissue of a human body part (e.g., a finger, a toe, an arm, a leg, a foot, and/or an internal organ, among other examples). For example, when the subject 104 is multi-layered tissue of a human body part, such as an arm, the subject 104 may comprise a first layer 120-1 (e.g., an epidermis layer), a second layer 120-2 (e.g., an upper dermis layer), a third layer 120-3 (e.g., a dermis plexus superficialis layer), a fourth layer 120-4 (e.g., a second dermis layer), a fifth layer 120-5 (e.g., a dermis plexus profundus layer), and/or sixth layer 120-6 (e.g., a subcutaneous tissue layer). A respective thickness of each layer may be, for example, 0.1 millimeters for the first layer 120-1, 0.2 millimeters for the second layer 120-2, 0.2 millimeters for the third layer 120-3, 0.9 millimeters for the fourth layer 120-4, 0.6 millimeters for the fifth layer 120-5, and 5.0 millimeters for the sixth layer 120-6. Accordingly, for this example, a total thickness associated with the first layer 120-1 may be 0.1 millimeters, a total thickness associated with the first layer 120-1 and the second layer 120-2 may be 0.3 millimeters, a total thickness associated with the first layer 120-1 through the third layer 120-3 may be 0.5 millimeters, a total thickness associated with the first layer 120-1 through the fourth layer 120-4 may be 1.4 millimeters, a total thickness associated with the first layer 120-1 through the fifth layer 120-5 may be 2.0 millimeters, and a total thickness associated with the first layer 120-1 through the sixth layer 120-6 may be 7.0 millimeters.

When the light enters the subject 104 from emission optic 110, a first portion of the light may be absorbed by the one or more layers 120, a second portion of the light may scatter throughout the one or more layers 120, and/or a third portion of the light may scatter throughout the one or more layers 120 and may be directed to the collection optic 112 (e.g., as further described below in relation to FIGS. 2A-2B, 3A-3C, and 4A-4D). The third portion of light may propagate to the collection optic 112 over a period of time. For example, a first part of the third portion of light may scatter and propagate through the first layer 120-1 to the collection optic 112 in a first time range and a second part of the third portion of light may scatter and propagate through the first layer 120-1 and at least the second layer 120-2 (e.g., from the first layer 120-1, to the second layer 120-2, and back through the first layer 120-1) in a second time range. Accordingly, light may transmit to the collection optic 112 at different times.

The collection optic 112 may include a lens, a window, an optical diffuser, an optical filter, an aperture stop, a reflective optical element, a diffractive optical element, a refractive optical element, and/or the like. In some implementations, the collection optic 112 may be configured to receive light from the subject 104 and to direct the light to the optical filter 114. The collection optic 112 may be proximate to the subject 104 (e.g., close to the subject 104) to allow the light to transmit from the subject 104 to the optical filter 114 (or directly to the optical sensor 116 when the optical sensor device 102 does not include the optical filter 114). As further shown in FIG. 1A, the barrier 118 may be provided between an emission section of the optical sensor device 102 (e.g., that includes the light source 108 and/or the emission optic 110) and a collection section of the optical sensor device 102 (e.g., that includes the collection optic 112, the optical filter

114, and/or the optical sensor 116). This may reduce interference from light that is not transmitted through the subject 104 to the optical sensor 116 via the collection optic 112 and/or the optical filter 114.

The optical filter 114 may include a spectral filter, a multispectral filter, an optical interference filter, a bandpass filter, a blocking filter, a long-wave pass filter, a short-wave pass filter, a dichroic filter, a linear variable filter (LVF), a circular variable filter (CVF), a Fabry-Perot filter (e.g., a Fabry-Perot cavity filter), a Bayer filter, a plasmonic filter, a photonic crystal filter, a nanostructure and/or metamaterial filter, an absorbent filter (e.g., comprising organic dyes, polymers, glasses, and/or the like), and/or the like. In some implementations, the optical filter 114 may include an array of optical channels. An optical channel, of the array of optical channels, may be disposed over a sensor element 122 of the optical sensor 116 and may be configured to pass light associated with a particular wavelength range to the sensor element 122 and/or to prevent light associated with at least one other wavelength range from passing to the sensor element 122. For example, the optical channel may be configured to pass light associated with a wavelength range of 1050 to 1150 nanometers (e.g., greater than or equal to 1050 nanometers and less than 1150 nanometers) and to block light associated with a wavelength range of 500 to 1050 nanometers (e.g., to block light associated with a wavelength that is greater than or equal 500 nanometers and less than 1050 nanometers).

In some implementations, the optical sensor 116 may include one or more sensor elements 122 (e.g., an array of sensor elements, also referred to herein as a sensor array), each configured to obtain information. For example, a sensor element 122 may provide an indication of intensity of light that is incident on the sensor element 122 (e.g., active/inactive or a more granular indication of intensity). As another example, a sensor element 122 may provide an indication of a wavelength or wavelength range of light that is incident on the sensor element 122 (e.g., red light, blue light, green light, ultraviolet light, infrared light, and/or the like). The optical sensor 116 may be configured to receive and/or collect respective information from the one or more sensor elements 122 to generate sensor data.

Figure 1B:
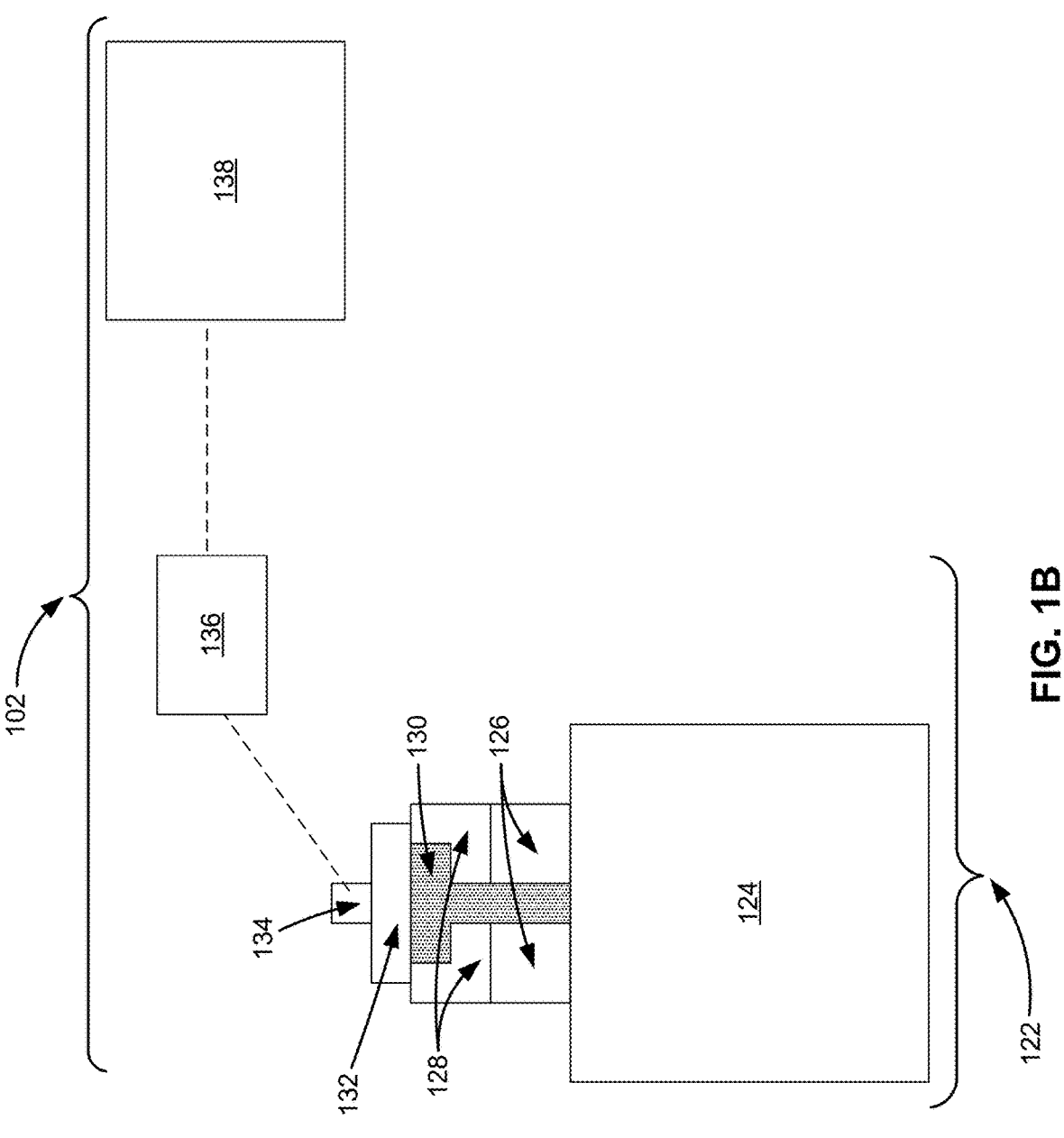

As shown in FIG. 1B, a sensor element 122 may include one or more components, such as a photodiode 124, a modulation gate 126, a charge-transfer assisting gate 128, a storage diode 130, a transfer gate 132, a floating diffusion 134, and/or a converter 136, among other examples. In some implementations, the one or more sensor elements 122 may be configured to operate in a gated mode. For example, the photodiode 124 may be configured to capture light (e.g., that is associated with a particular wavelength range) and generate a photocurrent. The modulation gate 126 may be configured to transfer the photocurrent to the storage diode 130, which may be configured to accumulate charge associated with the photocurrent. The charge-transfer assisting gate 128 and/or the transfer gate 132 may be configured to transfer the accumulated charge to the floating diffusion 134, which may be configured to store and provide the accumulated charge to the converter 136. The converter 136 may be configured to convert the accumulated charge into a voltage value, which is also referred to as an optical measurement (e.g., as further described herein).

In some implementations, the charge-transfer assisting gate 128 and/or the transfer gate 132 may be configured to transfer the accumulated charge (e.g., from the storage diode 130 to the floating diffusion 134) based on a transfer cycle. For example, the charge-transfer assisting gate 128 and/or the transfer gate 132 may be configured to transfer the accumulated charge on a periodic basis. The period of the of the transfer cycle may satisfy (e.g., may be less than) a transfer cycle period threshold, such as 10 nanoseconds. Accordingly, the converter 136 may convert the accumulated charge to generate an optical measurement based on the transfer cycle (e.g., generate an optical measurement based on the period of the transfer cycle).

As further shown in FIG. 1B, the optical sensor device 102 may comprise one or more processors 138, which are described in more detail below in connection with FIGS. 5 and 6. In some implementations, the optical sensor 116 may provide sensor data to the one or more processors 138. The sensor data may include respective optical measurements determined by the one or more sensor elements 122, as further described herein in relation to FIGS. 1C-1E.

Figure 1C:
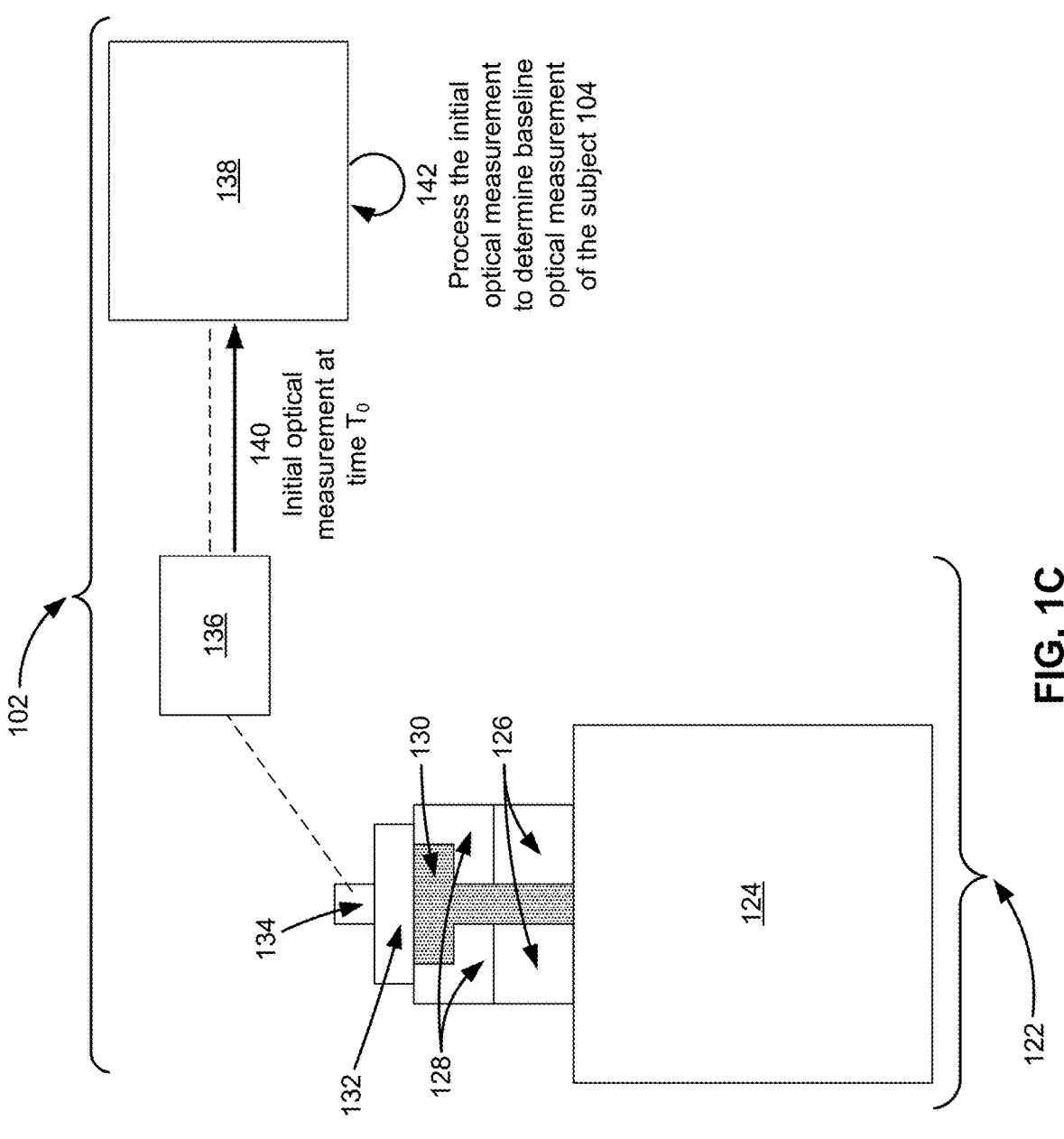

As shown in FIG. 1C, and by reference number 140, a sensor element 122 may provide an initial optical measurement (e.g., at time $T_0$) to the one or more processors 138 (e.g., as part of sensor data that is provided to the one or more processors 138 by the optical sensor 116). The sensor element 122 may be configured to generate and/or determine an optical measurement related to light associated with a particular wavelength. For example, the sensor element 122 may be disposed under an optical channel of the optical filter 114 that is configured to pass light associated with the particular wavelength to the sensor element 122 and/or the sensor element 122 may be configured to sense light associated with the particular wavelength. The initial optical measurement may indicate an amount of light (e.g., a number of photons) associated with the particular wavelength that the sensor element 122 accumulated at an initial time (e.g., at time $T_0$). For example, the initial optical measurement may indicate an amount of light associated with the particular wavelength that sensor element 122 accumulated at a time after the sensor element 122 had been refreshed and/or reset. As another example, the initial optical measurement may indicate an amount of light associated with the particular wavelength that sensor element 122 accumulated at a time (e.g., at time $T_0$) when the light source 108 begins to emit light (e.g., before the emitted light propagates through the subject 104 to the sensor element 122).

As further shown in FIG. 1C, and by reference number 142, the one or more processors 138 may process the initial optical measurement. For example, the one or more processors 138 may process the initial optical measurement to determine a baseline optical measurement of the subject 104. The baseline optical measurement may indicate an amount of ambient light associated with the particular wavelength that transmitted through the subject to the sensor element 122 (e.g., before light emitted by the light source 108 propagates through the subject 104 to the sensor element 122).

Figure 1D:
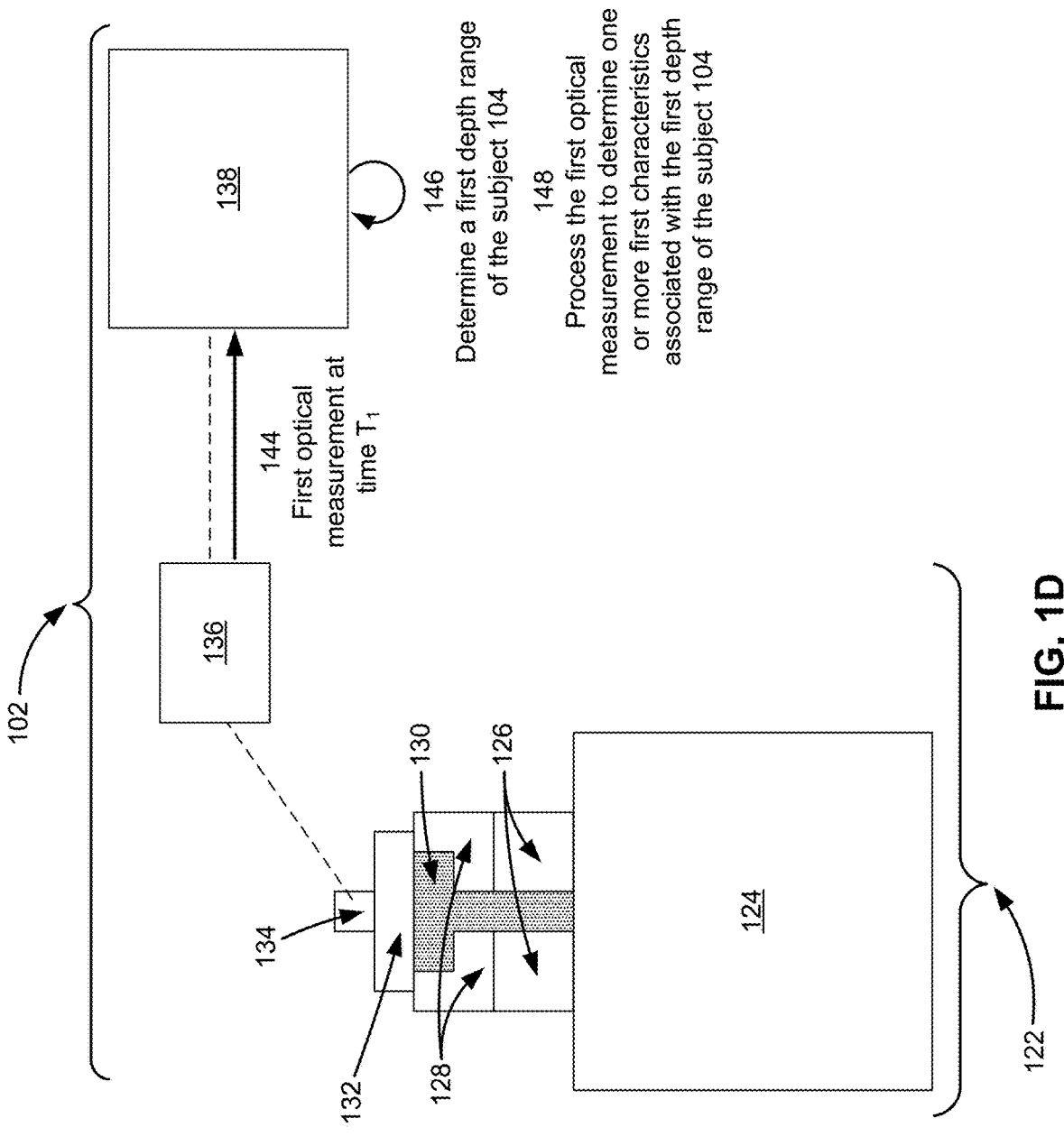

As shown in FIG. 1D, and by reference number 144, the sensor element 122 may provide a first optical measurement (e.g., at time $T_1$) to the one or more processors 138. The first optical measurement may indicate an amount of light associated with the particular wavelength that the sensor element 122 accumulated during a first time range. For example, the first time range may include a time range between time $T_0$ and time $T_1$ (e.g., times after time $T_0$ and before time $T_1$). The first time range may correspond to a time range when the light source 108 emits light, or has emitted light, and at least some of the light propagates through the subject 104 to the sensor element 122).

As further shown in FIG. 1D, and by reference number 146, the one or more processors 138 may determine, based on the particular wavelength range and the first time range (e.g., a duration of the first time range), that the first optical measurement is related to a first depth range of the subject 104. For example, the one or more processors 138 may determine an amount of elapsed time since light was emitted (e.g., a difference between time $T_1$ and time $T_0$) and may search, based on the amount of elapsed time, a data structure (e.g., a table, a database, and/or an electronic file, among other examples, that is associated with and/or accessible to the one or more processors 138) to determine the first depth range of the subject 104. The data structure may indicate respective estimated propagation depths of light associated with the particular wavelength in the subject 104 (or in a representative subject) for different amounts of elapsed time.

In some implementations, when the subject 104 comprises multiple layers, the one or more processors 138 may determine (e.g., based on the first depth range) that the first optical measurement is related to the first layer 120-1 of the subject 104. For example, when the subject 104 comprises multi-layered tissue of a mammalian body part, the one or more processors 138 may determine that a thickness of the first depth range is less than 0.1 millimeters, and may therefore determine that the first optical measurement is related to an epidermis layer (e.g., the first layer 120-1) of the subject 104.

As further shown in FIG. 1D, and by reference number 148, the one or more processors 138 may process (e.g., using one or more computational algorithms) the first optical measurement to determine one or more first characteristics associated with the first depth range of the subject 104, such as an absorption characteristic that indicates an amount of light (e.g., that is associated with the particular wavelength range) that is absorbed within the first depth range, and/or a scatter characteristic that indicates an amount of light (e.g., that is associated with the particular wavelength range) that is scattered by the first depth range, among other examples. In some implementations, when the subject 104 comprises multiple layers, the one or more processors 138 may process the first optical measurement to determine one or more first characteristics of the first layer 120-1 of the subject 104. For example, when the subject 104 comprises multi-layered tissue of a mammalian body part and the first layer 120-1 is an epidermis layer of the subject 104, the one or more processors 138 may process the first optical measurement to determine an absorption characteristic and/or a scatter characteristic associated with the epidermis layer (e.g., the first layer 120-1) of the subject 104.

In some implementations, the one or more processors 138 may modify the first optical measurement based on the initial optical measurement before processing the first optical measurement. For example, the one or more processors 138 may subtract the initial optical measurement from the first optical measurement. In this way, the one or more processors 138 may remove information from the first optical measurement that is associated with a time before the initial time (e.g., time $T_0$). Accordingly, the one or more processors 138 may process the first optical measurement to determine one or more first characteristics of the first depth range and/or the first layer 120-1 based on light that is emitted by the light source 108 at the initial time.

Figure 1E:
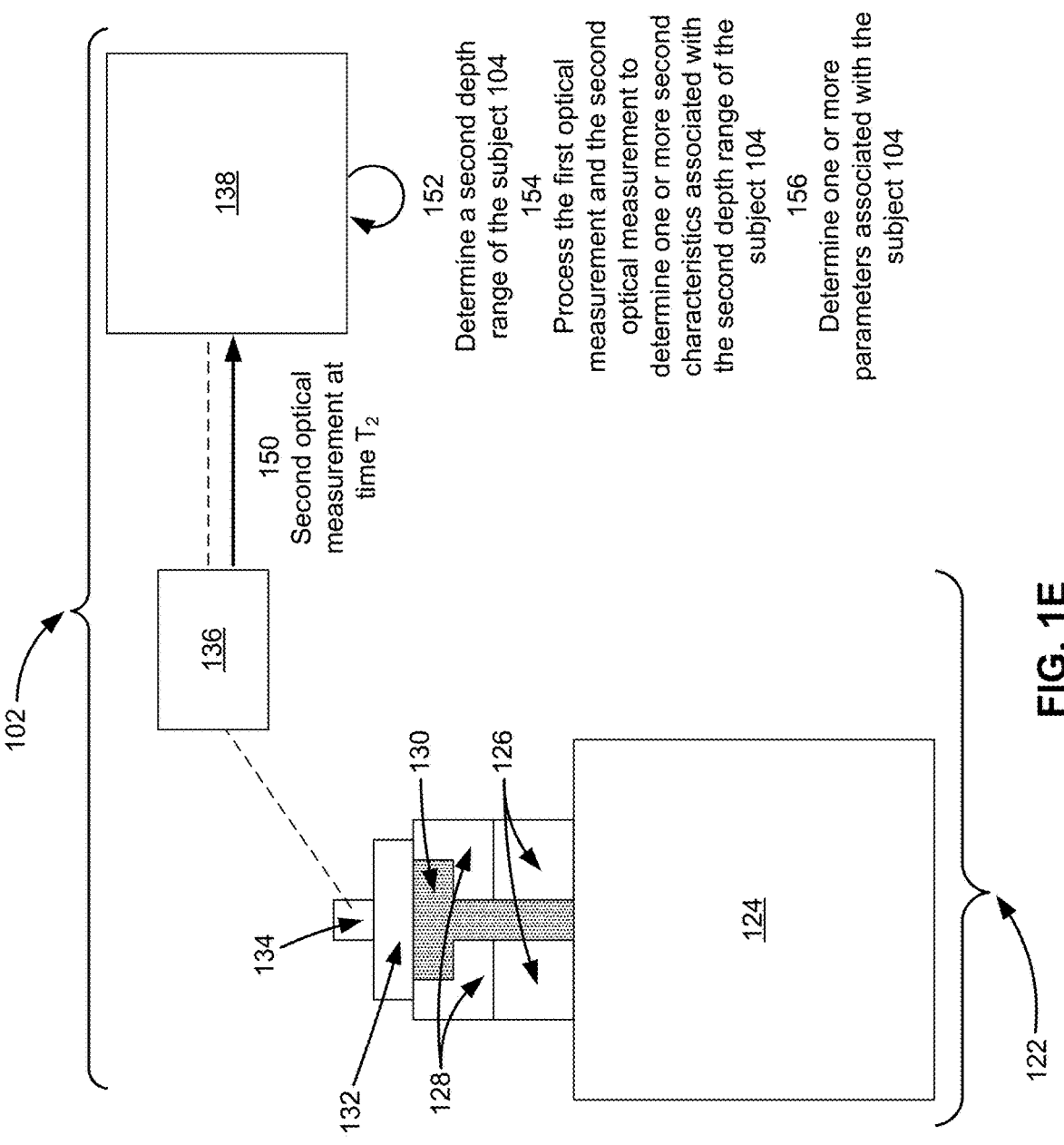

As shown in FIG. 1E, and by reference number 150, the sensor element 122 may provide a second optical measurement (e.g., at time $T_2$) to the one or more processors 138. The second optical measurement may indicate an amount of light associated with the particular wavelength that the sensor element 122 accumulated during a second time range (e.g., where the first time range is a subrange of the second time range). For example, the second time range may include a time range between time $T_0$ and time $T_2$ (e.g., times after time $T_0$ and less and before time $T_2$). The second time range may correspond to a time range when the light source 108 emits light, or has emitted light, and at least some of the light propagates through the subject 104 to the sensor element 122).

As further shown in FIG. 1E, and by reference number 152, the one or more processors 138 may determine, based on the particular wavelength range and the second time range (e.g., a duration of the second time range), that the second optical measurement is related to the first depth range and a second depth range (e.g., where the second depth range does not overlap with the first depth range) of the subject 104. For example, the one or more processors 138 may determine an amount of elapsed time since light was emitted by the light source 108 (e.g., a difference between time $T_2$ and time $T_0$) and may search, based on the amount of elapsed time, the data structure described above to determine the first depth range and/or the second depth range of the subject 104. The one or more processors 138 may determine that the second optical measurement is related to the first depth range and the second depth range because the emitted light propagates from the light source 108, through the emission optic 110, through the first depth range of the subject 104, through the second depth range of the subject 104, through the first depth range of the subject 104 (again), through the collection optic 112 and/or the optical filter 114, to the sensor element 122.

In some implementations, when the subject 104 comprises multiple layers, the one or more processors 138 may determine (e.g., based on the first depth range and the second depth range) that the second optical measurement is related to the first layer 120-1 and the second layer 120-2 of the subject 104. For example, when the subject 104 comprises multi-layered tissue of a mammalian body part, the one or more processors 138 may determine that a total thickness of the first depth range and the second depth range is less than 0.3 millimeters and may therefore determine that the second optical measurement is related to an epidermis layer (e.g., the first layer 120-1) and an upper dermis layer (e.g., the second layer 120-2) of the subject 104.

As further shown in FIG. 1E, and by reference number 154, the one or more processors 138 may process (e.g., using one or more computational algorithms) the first optical measurement and the second optical measurement to determine one or more second characteristics associated with the second depth range of the subject 104. For example, the one or more processors 138 may determine a difference between the first optical measurement and the second optical measurement to determine a delta optical measurement. Accordingly, the delta optical measurement may indicate an amount of light associated with the particular wavelength that the sensor element 122 accumulated from the ending of the first time range (e.g., time $T_1$) to the ending of the second time range (e.g., time $T_2$) (e.g., a time after time $T_1$ and before time $T_2$). The one or more processors 138 may process the delta optical measurement to determine an absorption characteristic and/or a scatter characteristic, among other examples, of the second depth range of the subject 104.

In some implementations, when the subject 104 comprises multiple layers, the one or more processors 138 may process the first optical measurement and the second optical measurement to determine one or more second characteristics of the second layer 120-2 of the subject 104. For example, when the subject 104 comprises multi-layered tissue of a mammalian body part, the first layer 120-1 is an epidermis layer of the subject 104, and the second layer 120-2 is an upper dermis layer of the subject 104, the one or more processors 138 may process the first optical measurement and the second optical measurement (e.g., in a similar manner as that described above) to determine an absorption characteristic and/or a scatter characteristic, among other examples, associated with the upper dermis layer (e.g., the second layer 120-2) of the subject 104.

In some implementations, the sensor element 122 may provide optical measurements (e.g., the initial optical measurement, the first optical measurement, and/or the second optical measurement, as described herein in relation to FIGS. 1C-1E) to the one or more processors 138 based on the transfer cycle of the sensor element 122 (e.g., as described herein in relation to FIG. 1B). Accordingly, the sensor element 122 may provide individual optical measurements (e.g., as part of sensor data) to the one or more processors 138 on a periodic basis that is based on the period of the transfer cycle (e.g., that is less than 10 nanoseconds). Further, when the first time range is a subrange of the second time range, a difference between an ending time of the first time range and an ending time of the second time range may match (e.g., within a tolerance) the period of the transfer cycle. Accordingly, in some implementations, the difference may satisfy (e.g., may be less than) a transfer cycle period threshold, such as 10 nanoseconds.

As further shown in FIG. 1E, and by reference number 156, the one or more processors 138 may determine one or more parameters associated with the subject 104. In some implementations, the one or more processors 138 may process (e.g., using one or more computational algorithms) the one or more first characteristics associated with the first depth range of the subject 104 and/or the one or more second characteristics associated with the second depth range of the subject 104 to determine the one or more parameters associated with the subject 104. For example, the one or more processors 138 may use one or more computational algorithms to compare the one or more first characteristics and/or the one or more second characteristics to determine whether the first depth range of the subject 104 is molecularly similar to the second depth range of the subject 104.

In some implementations, when the subject 104 comprises multiple layers, the one or more processors 138 may process (e.g., using one or more computational algorithms) the one or more first characteristics of the first layer 120-1 (e.g., an epidermis layer) and the one or more second characteristics of the second layer 120-2 (e.g., an upper dermis layer) to determine the one or more parameters associated with the subject 104. For example, when the subject 104 comprises multi-layered tissue of a mammalian body part, the one or more processors 138 may process the one or more first characteristics and/or the one or more second characteristics to determine one or more health parameters associated with the subject 104. The one or more health parameters may include, for example, a cardiac output parameter, a respiration rate parameter, a vascular disease parameter, an arterial compliance parameter, an endothelial function parameter, a venous condition assessment parameter, a vasospastic condition parameter, a microvascular flow parameter, a tissue viability parameter, an autonomic function parameter, a vasomotor function parameter, a thermoregulation parameter, an orthostasis parameter, a vasoconstriction parameter, a body fat composition parameter, a food sensitivity response parameter, a pharmaceutical sensitivity response parameter, a skin coloring or tanning response parameter, an electrolyte level parameter, a carbon monoxide level parameter, a hydration level parameter, a blood glucose level parameter, a blood pressure parameter, a blood oxygen parameter, and/or a heart rate parameter.

In some implementations, the one or more processors 138 may provide information indicating the one or more parameters associated with the subject 104. For example, the one or more processors 138 may cause display of the information on a display screen associated with the optical sensor device 102 (e.g., a display screen of the optical sensor device 102 and/or a display screen of a user device that communicates with the optical sensor device 102). When the display screen is included in the optical sensor device 102, the one or more processors 138 may send the information to the display screen to cause the display screen to display the information. When the display screen is included in the user device, the one or more processors 138 may send the information to the user device to cause the user device to display the information on the display screen of the user device.

While some implementations described herein in relation to FIGS. 1C-1E are directed to an individual sensor element 122 providing optical measurements at particular times (e.g., time $T_0$, time $T_1$, and time $T_2$), implementations include multiple sensor elements providing respective optical measurements (e.g., that are associated with different wavelength ranges) to the one or more processors 138 at the particular times as part of sensor data. Accordingly, the one or more processors 138 may process a set of initial optical measurements to determine a set of baseline optical measurements (e.g., in a similar manner as that described herein in relation to FIG. 1C), may process a set of first optical measurements to determine one or more first characteristics associated with a first depth range of the subject 104 (e.g., in a similar manner as that described herein in relation to FIG. 1D), and/or may process the set of first optical measurements and a set of second optical measurements to determine one or more second characteristics associated with a second depth range of the subject 104 (e.g., in a similar manner as that described herein in relation to FIG. 1E). The one or more processors 138 then may process the one or more first characteristics associated with the first depth range of the subject 104 and/or the one or more second characteristics associated with the second depth range of the subject 104 to determine one or more parameters associated with the subject 104 (e.g., in a similar manner as that described herein in relation to FIG. 1E).

As indicated above, FIGS. 1A-1E are provided merely as one or more examples. Other examples may differ from what is described with regard to FIGS. 1A-1E.

Figure 2A:
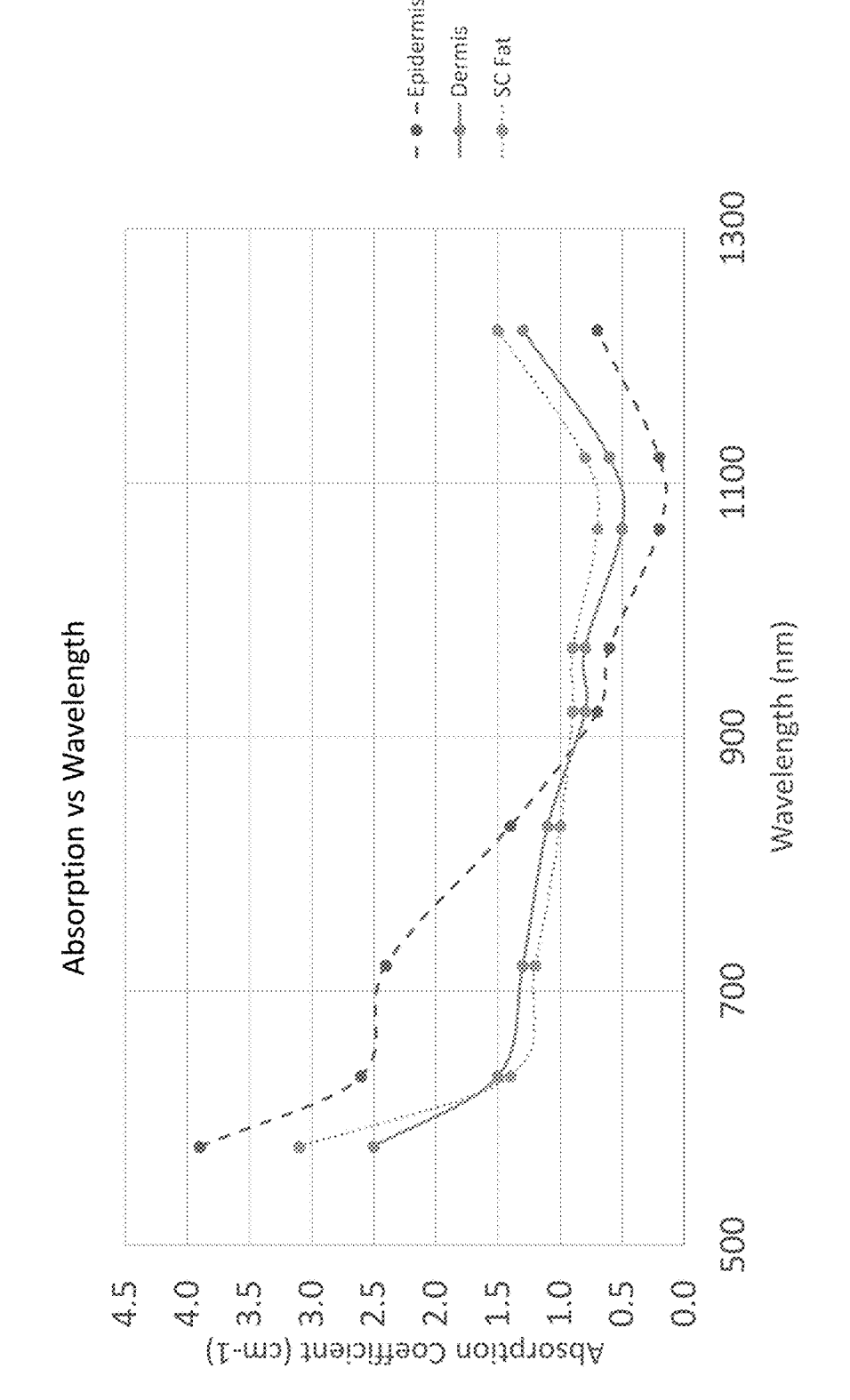
FIGS. 2A-2B are diagrams of optical characteristics associated with different layers of a multi-layered subject described herein.
Figure 2B:
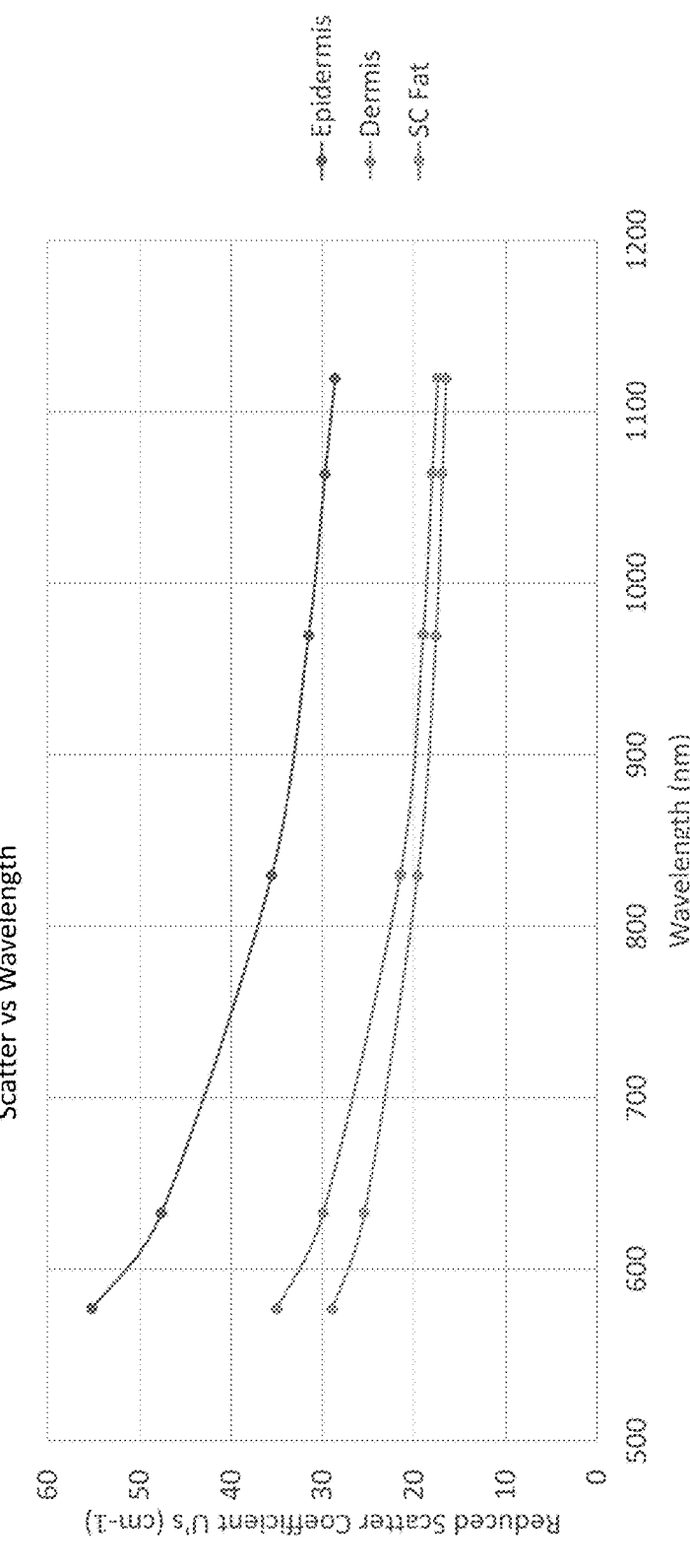

FIGS. 2A-2B are diagrams 200 of optical characteristics associated with different layers of a multi-layered subject 104 described herein. FIG. 2A shows an absorption coefficient (measured in centimeter$^{-1}$) associated with an epidermis layer (e.g., the first layer 120-1 in FIG. 1A), an upper dermis layer (e.g., the second layer 120-2 in FIG. 1A), and a subcutaneous tissue layer (e.g., the sixth layer 120-6 in FIG. 1A) of the subject 104. As shown in FIG. 2A, each layer has a maximum absorption coefficient for light that is associated with a wavelength of approximately 575 nanometers and a minimum absorption coefficient for light that is associated with a wavelength range of approximately 1050 to 1150 nanometers.

FIG. 2B shows a reduced scatter coefficient (measured in centimeter$^{-1}$) associated with the epidermis layer (e.g., the first layer 120-1 in FIG. 1A), the upper dermis layer (e.g., the second layer 120-2 in FIG. 1A), and the subcutaneous tissue layer (e.g., the sixth layer 120-6 in FIG. 1A) of the subject 104. As shown in FIG. 2B, each layer has a maximum reduced scatter coefficient for light that is associated with a wavelength of approximately 575 nanometers. Further, the reduced scatter coefficient has an indirect relationship with light wavelength. Accordingly, as shown in FIG. 2B, the reduced scatter coefficient decreases for each layer as the light wavelength increases.

As indicated above, FIGS. 2A-2B are provided merely as one or more examples. Other examples may differ from what is described with regard to FIGS. 2A-2B.

Figure 3A:
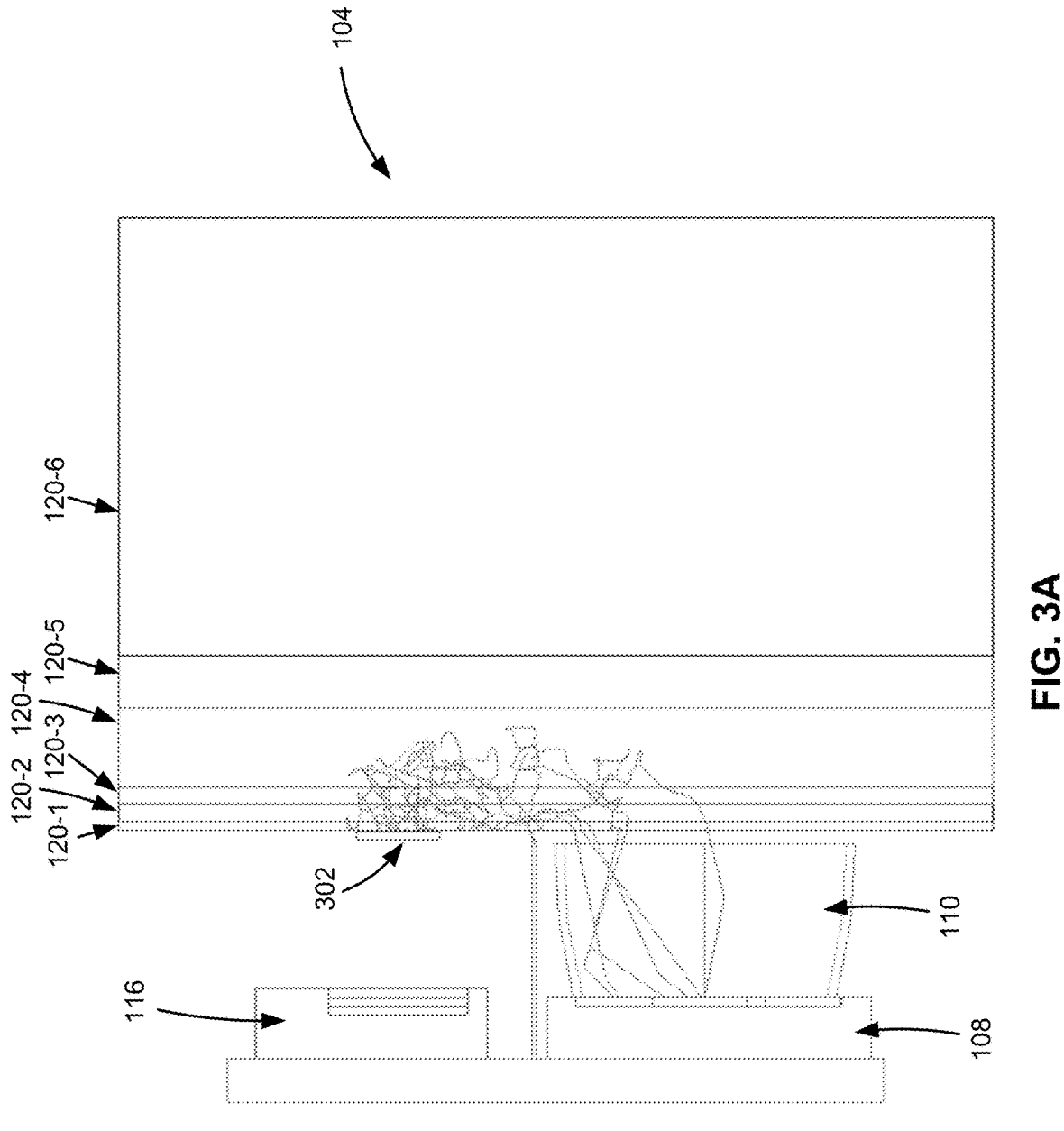
FIGS. 3A-3C are diagrams illustrating ray paths of light propagating through one or more layers of a multi-layered subject described herein.
Figure 3B:
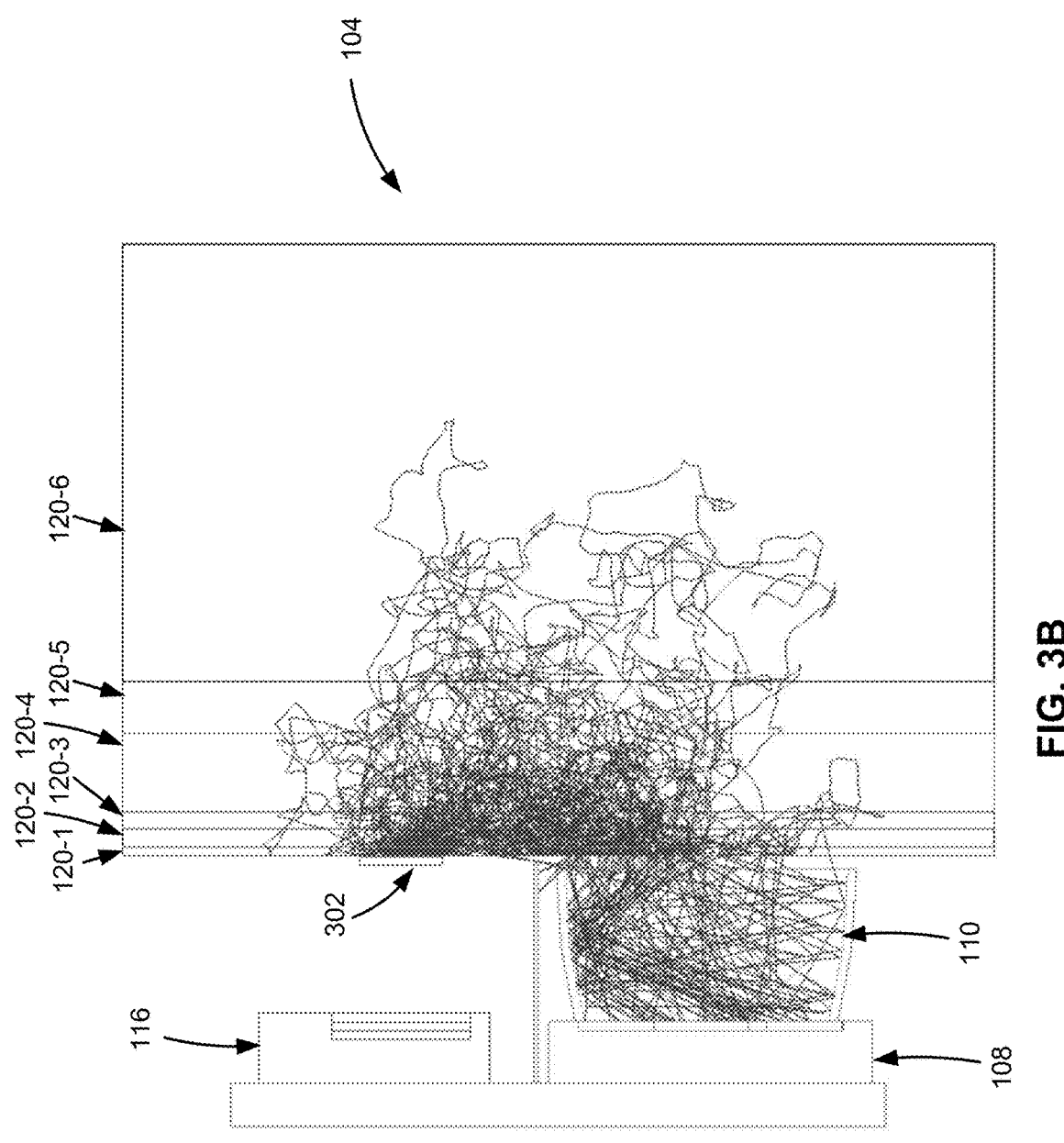
Figure 3C:
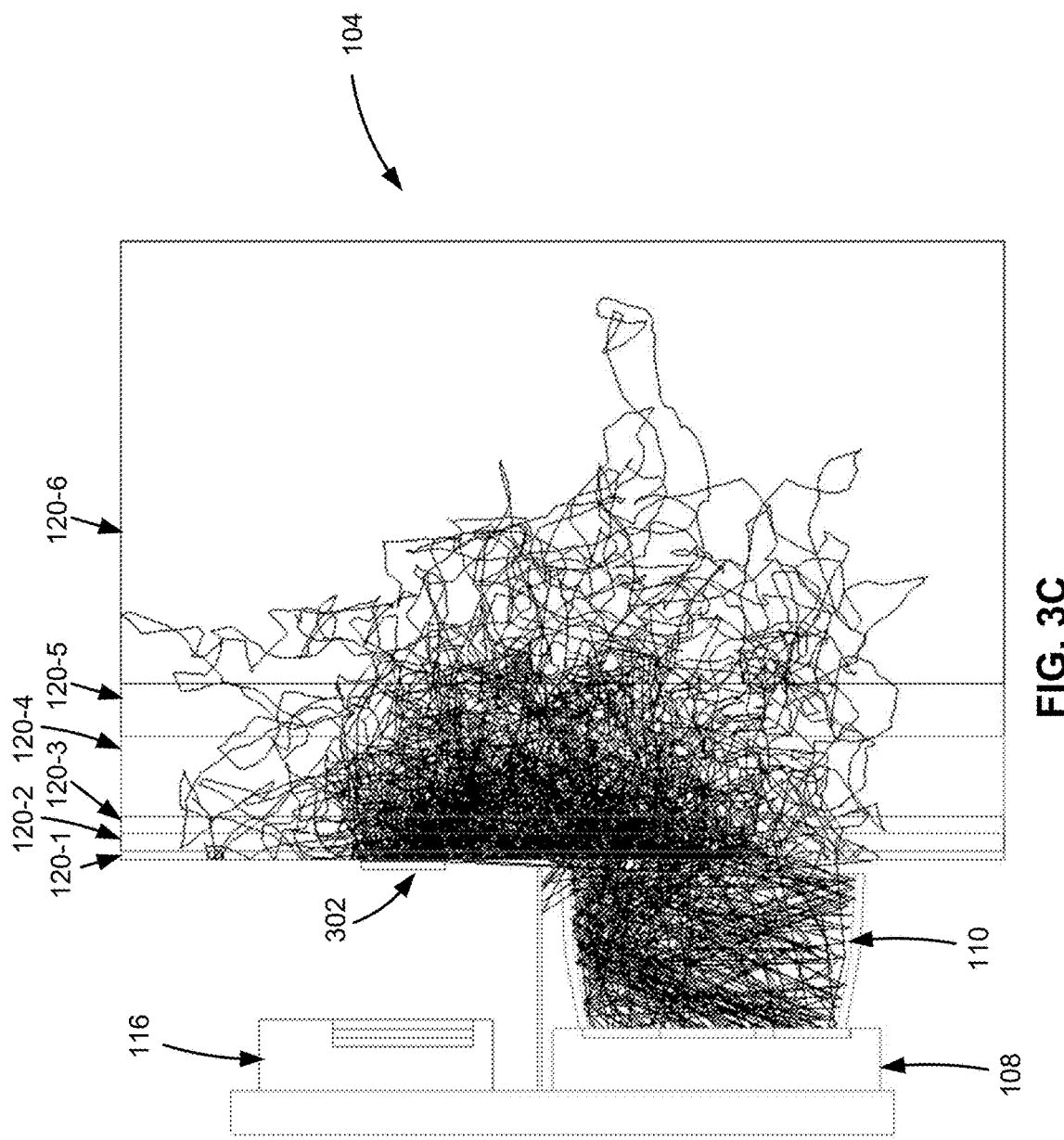

FIGS. 3A-3C are diagrams 300 illustrating ray paths of light propagating through one or more layers 120 of a multi-layered subject 104 (e.g., multi-layered tissue of a mammalian body part) described herein. FIGS. 3A-3C show light associated with respective wavelengths emitting from a light source 108 of an optical sensor device 102, propagating through an emission optic 110 to a subject 104, and propagating through one or more layers 120 of the subject 104 to a collection surface 302 of the optical sensor device 102. The collection surface may be associated with the collection optic 112 and/or the optical filter 114 and may be configured to allow the light to propagate to the optical sensor 116.

As shown in FIG. 3A, light associated with a wavelength of approximately 575 nanometers that penetrates a first layer 120-1 (e.g., an epidermis layer) through a fourth layer 120-4 (e.g., a second dermis layer) of the subject 104 may propagate to the collection surface 302. As shown in FIG. 3B, light associated with a wavelength of approximately 700 nanometers that penetrates the first layer 120-1 (e.g., the epidermis layer) through a sixth layer 120-6 (e.g., a subcutaneous tissue layer) of the subject 104 may propagate to the collection surface 302. As shown in FIG. 3C, light associated with a wavelength of approximately 1100 nanometers that penetrates the first layer 120-1 (e.g., the epidermis layer) through the sixth layer 120-6 (e.g., a subcutaneous tissue layer) of the subject 104 may propagate to the collection surface 302. As further shown in FIGS. 3B and 3C, the light associated with a wavelength of approximately 1100 nanometers may spread more in a lateral direction (e.g., perpendicular to an emission trajectory of the light from the light source 108) within the one or more layers 120 of the subject 104 than the light associated with a wavelength of approximately 700 nanometers. Accordingly, in some cases, light associated with a wavelength of approximately 1100 nanometers may penetrate more of the one or more layers 120 of the subject 104 than is penetrated using light associated with other wavelengths that are less 1100 nanometers.

As indicated above, FIGS. 3A-3C are provided merely as one or more examples. Other examples may differ from what is described with regard to FIGS. 3A-3C.

FIGS. 4A-4D are diagrams 400 illustrating relative sensor flux of an optical sensor 116 of an optical sensor device 102 in association with light that propagates through one or more layers 120 of a multi-layered subject 104 (e.g., a multi-layered tissue of a mammalian body part) described herein. FIGS. 4A-4D show the relative sensor flux of the optical sensor 116 for different lateral distances (e.g., a minimum spacing ("min spacing") of 2.5 millimeters, a nominal spacing ("nom spacing" 0 of 3.5 millimeters, and a maximum spacing ("max spacing") of 5.0 millimeters) between an output surface of a light source 108 of the optical sensor device 102 and an input surface of the optical sensor 116.

Figure 4A:
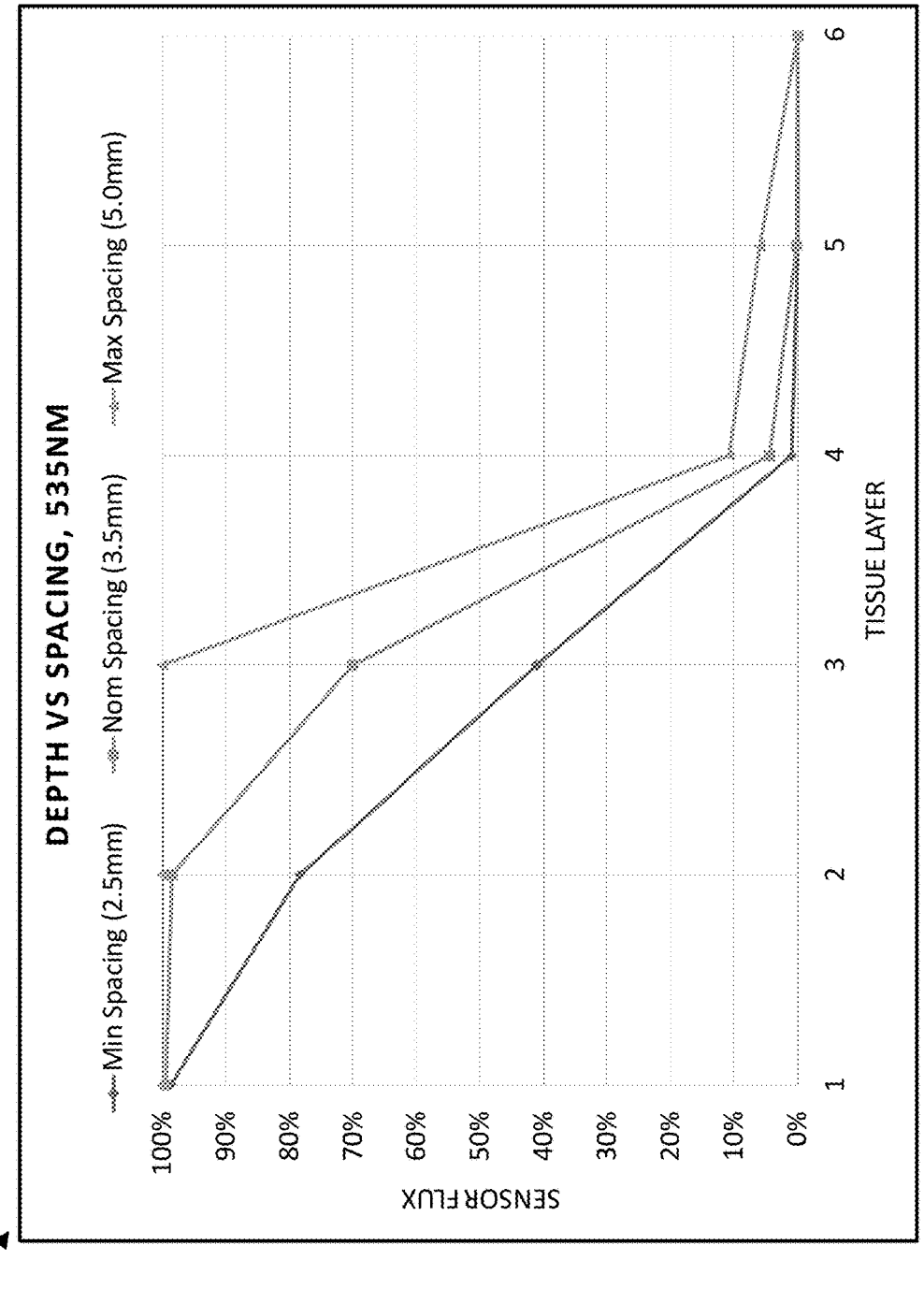
FIGS. 4A-4D are diagrams illustrating relative sensor flux of an optical sensor of an optical sensor device in association with light that propagates through one or more layers of a multi-layered subject described herein.
Figure 4B:
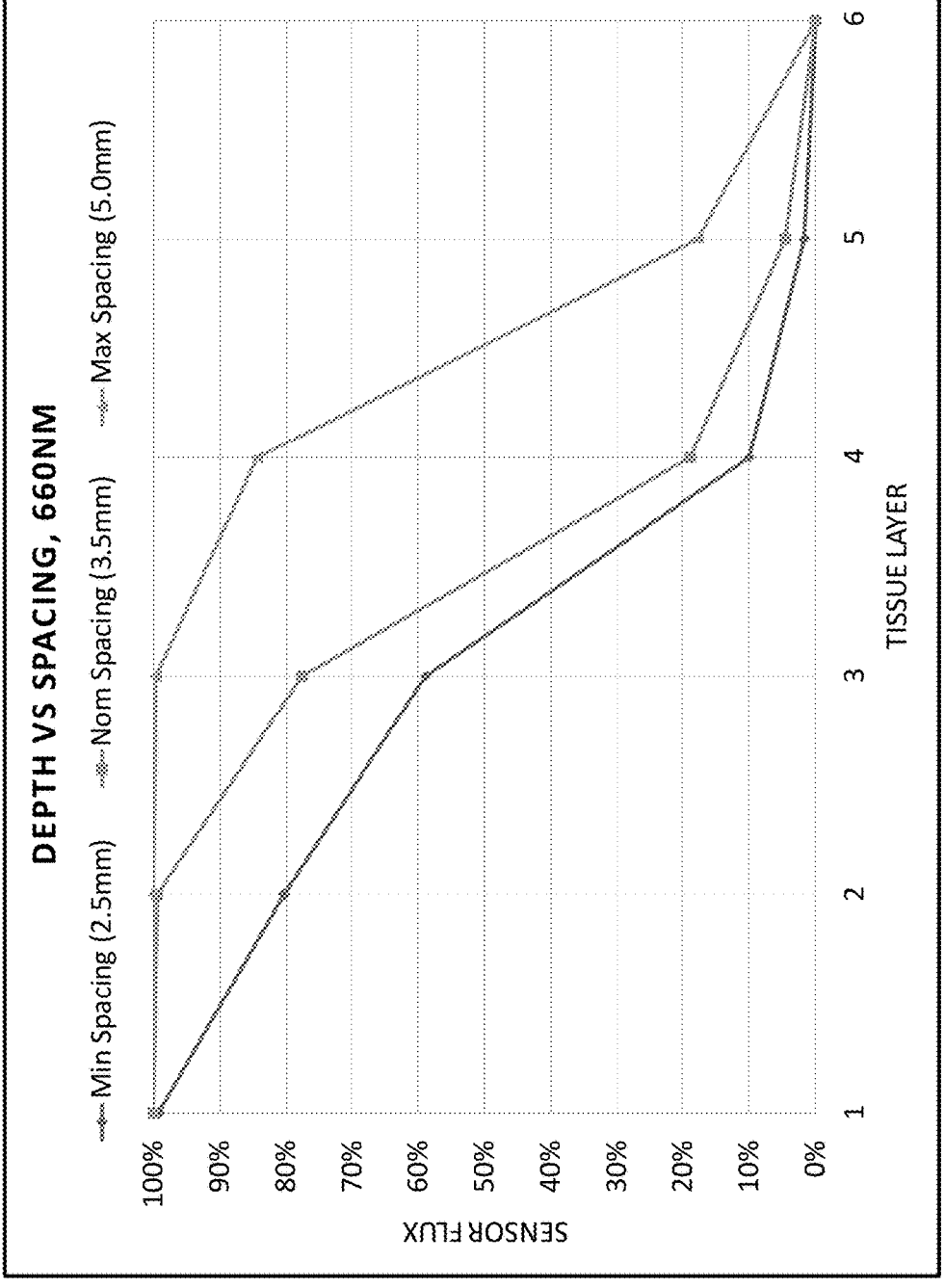
Figure 4C:
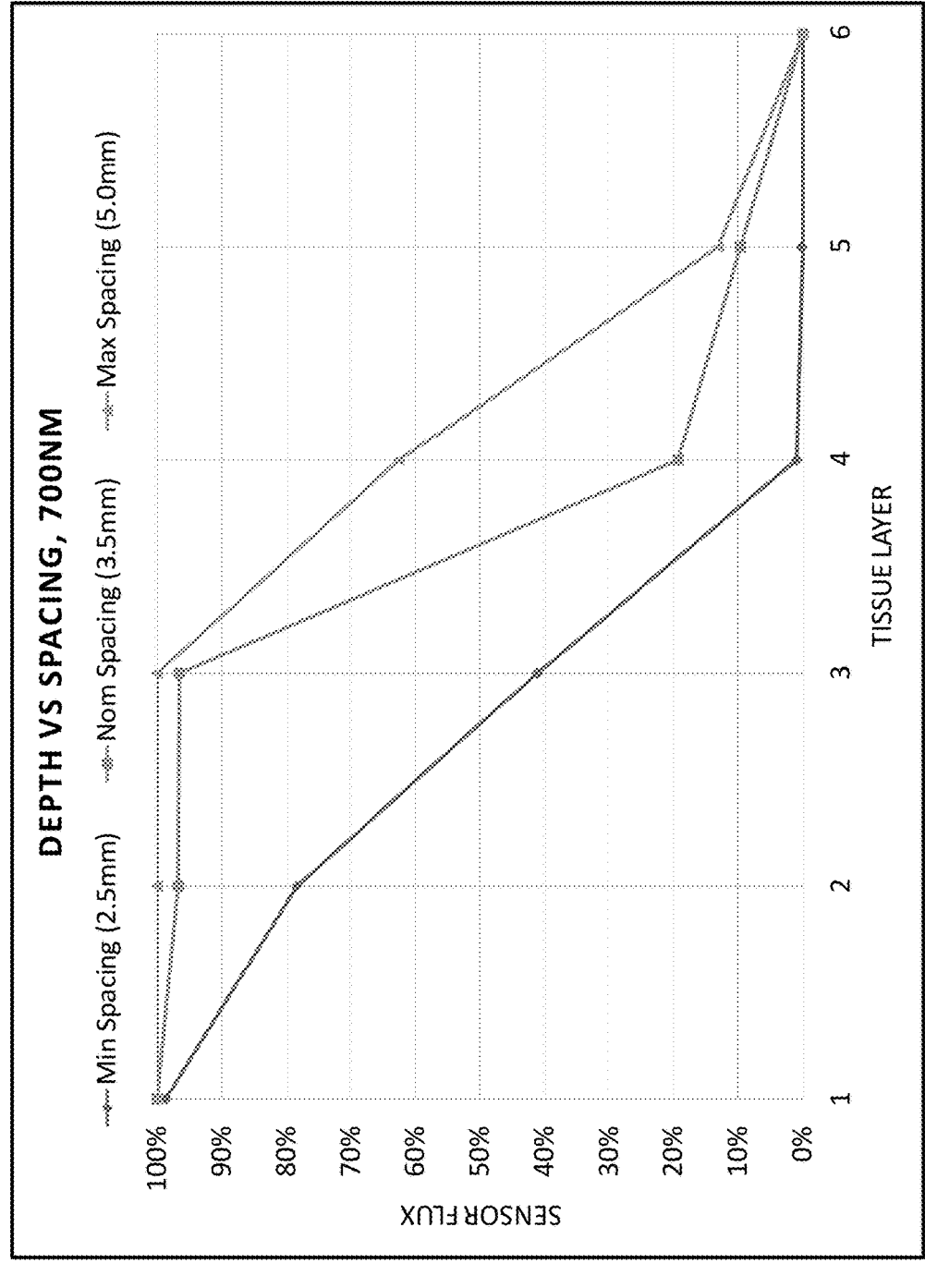
Figure 4D:
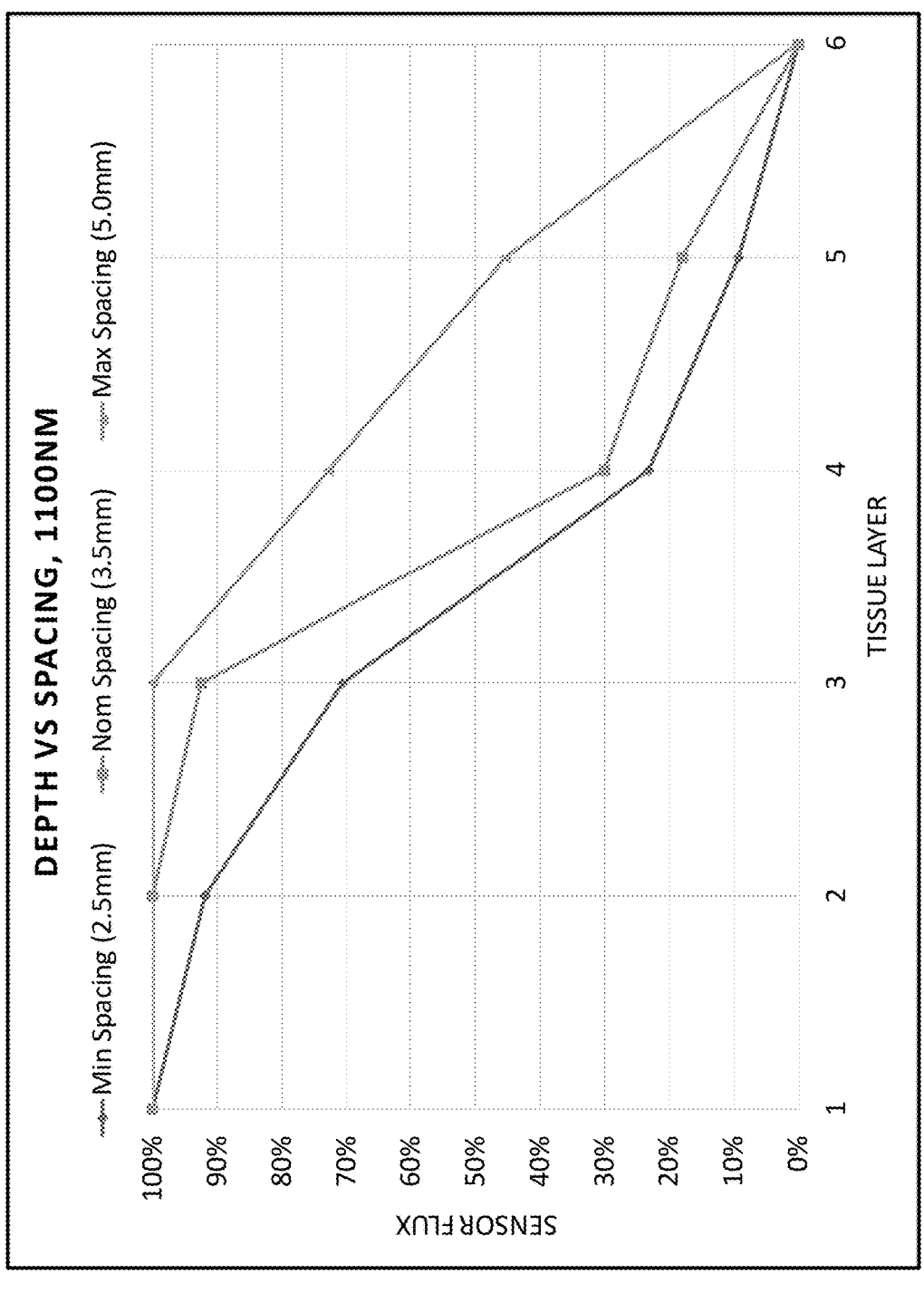

As shown in FIG. 4A, for light associated with a wavelength of approximately 535 nanometers that penetrates the first layer 120-1 through the sixth layer 120-6 of the subject 104, the relative sensor flux is highest when the lateral distance is 5.0 millimeters. As shown in FIG. 4B, for light associated with a wavelength of approximately 660 nanometers that penetrates the first layer 120-1 through the sixth layer 120-6 of the subject 104, the relative sensor flux is highest when the lateral distance is 5.0 millimeters. As shown in FIG. 4C, for light associated with a wavelength of approximately 700 nanometers that penetrates the first layer 120-1 through the sixth layer 120-6 of the subject 104, the relative sensor flux is highest when the lateral distance is 5.0 millimeters. As shown in FIG. 4D, for light associated with a wavelength of approximately 1100 nanometers that penetrates the first layer 120-1 through the sixth layer 120-6 of the subject 104, the relative sensor flux is highest when the lateral distance is 5.0 millimeters.

Accordingly, the optical sensor device 102 (e.g., as described above in relation to FIGS. 1A-1E) may be configured to cause the lateral distance between the output surface of the light source 108 and the input surface of the optical sensor 116 to satisfy (e.g., be greater than or equal to) a lateral distance threshold, such as 5.0 millimeters. In this way, the optical sensor device 102 may be configured to ensure an optimal sensor flux of the optical sensor 116 for light associated with various wavelengths.

As indicated above, FIGS. 4A-4D are provided as one or more examples. Other examples may differ from what is described with regard to FIGS. 4A-4D.

Figure 5:
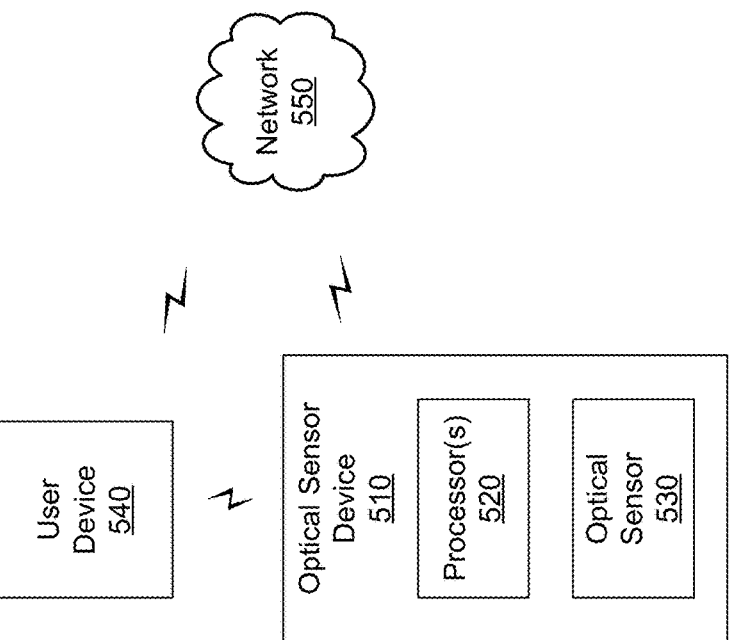
FIG. 5 is a diagram of an example environment in which systems and/or methods described herein may be implemented.

FIG. 5 is a diagram of an example environment 500 in which systems and/or methods described herein may be implemented. As shown in FIG. 5, environment 500 may include an optical sensor device 510 (e.g., that corresponds to the optical sensor device 102 described herein) that may include one or more processors 520 (e.g., that correspond to the one or more processors 138 described herein) and an optical sensor 530 (e.g., that corresponds to the optical sensor 116 described herein). The environment 500 may also include a user device 540 and a network 550. Devices of environment 500 may interconnect via wired connections, wireless connections, or a combination of wired and wireless connections.

Optical sensor device 510 may include an optical device capable of storing, processing, and/or routing image information and/or spectral information associated with a subject. For example, optical sensor device 510 may include a spectrometer device that performs spectroscopy, such as a spectral optical sensor device (e.g., a binary multispectral optical sensor device that performs vibrational spectroscopy (such as a near infrared (NIR) spectrometer), a mid-infrared spectroscopy (mid-IR), Raman spectroscopy, and/or the like). In another example, optical sensor device 510 may perform a health parameter determination. In this case, optical sensor device 510 may utilize the same wavelengths, different wavelengths, a combination of the same wavelengths and different wavelengths, and/or the like for such determinations. In some implementations, optical sensor device 510 may be incorporated into a user device 540, such as a wearable spectrometer and/or the like. In some implementations, optical sensor device 510 may receive information from and/or transmit information to another device in environment 500, such as user device 540.

Optical sensor device 510 may include one or more processors 520, described in more detail in connection with FIG. 6.

Optical sensor device 510 may include an optical sensor 530. Optical sensor 530 includes a device capable of sensing light. For example, optical sensor 530 may include an image sensor, a multispectral sensor, a spectral sensor, and/or the like. In some implementations, optical sensor 530 may include a silicon (Si) based sensor, an indium-gallium-arsenide (InGaAs) based sensor, a lead-sulfide (PbS) based sensor, or a germanium (Ge) based sensor, and may utilize one or more sensor technologies, such as a complementary metal-oxide-semiconductor (CMOS) technology, or a charge-coupled device (CCD) technology, among other examples. In some implementations, optical sensor 530 may include a front-side illumination (FSI) sensor, a back-side illumination (BSI) sensor, and/or the like. In some implementations, optical sensor 530 may be included in a camera of optical sensor device 510 and/or user device 540.

User device 540 includes one or more devices capable of receiving, generating, storing, processing, and/or providing the imaging information and/or the spectral information associated with the subject. For example, user device 540 may include a communication and/or computing device, such as a mobile phone (e.g., a smart phone, a radiotelephone, and/or the like), a computer (e.g., a laptop computer, a tablet computer, a handheld computer, and/or the like), a gaming device, a wearable communication device (e.g., a smart wristwatch, a pair of smart eyeglasses, and/or the like), or a similar type of device. In some implementations, user device 540 may receive information from and/or transmit information to another device in environment 500, such as optical sensor device 510.

Network 550 includes one or more wired and/or wireless networks. For example, network 550 may include a cellular network (e.g., a long-term evolution (LTE) network, a code division multiple access (CDMA) network, a 5G network, a 4G network, a 5G network, another type of next generation network, and/or the like), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

The number and arrangement of devices and networks shown in FIG. 5 are provided as an example. In practice, there may be additional devices and/or networks, fewer devices and/or networks, different devices and/or networks, or differently arranged devices and/or networks than those shown in FIG. 5. Furthermore, two or more devices shown in FIG. 5 may be implemented within a single device, or a single device shown in FIG. 5 may be implemented as multiple, distributed devices. For example, although optical sensor device 510 and user device 540 are described as separate devices, optical sensor device 510 and user device 540 may be implemented as a single device. Additionally, or alternatively, a set of devices (e.g., one or more devices) of environment 500 may perform one or more functions described as being performed by another set of devices of environment 500.

Figure 6:
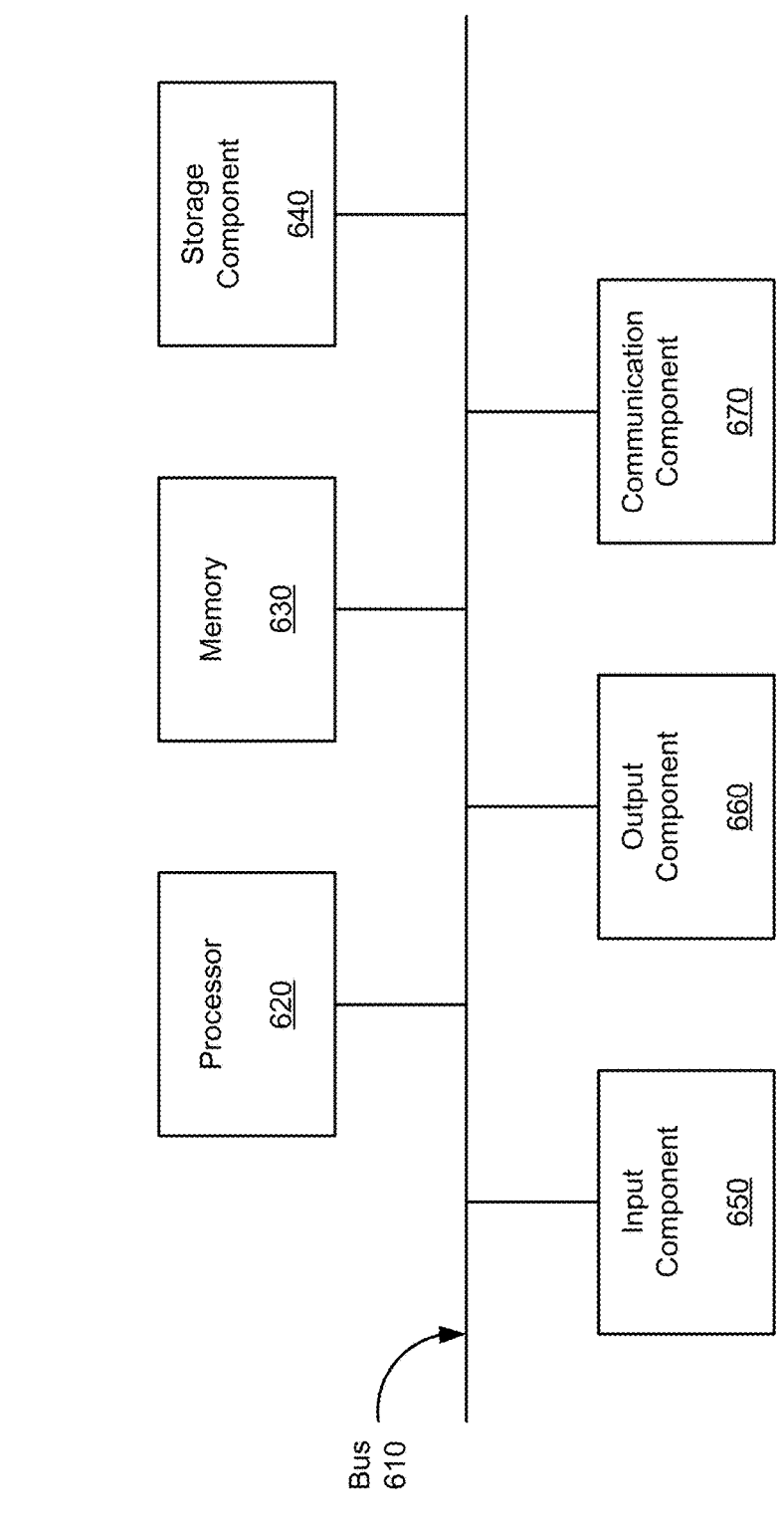
FIG. 6 is a diagram of example components of one or more devices of FIG. 5.

FIG. 6 is a diagram of example components of a device 600, which may correspond to optical sensor device 510 and/or user device 540. In some implementations, optical sensor device 510 and/or user device 540 may include one or more devices 600 and/or one or more components of device 600. As shown in FIG. 6, device 600 may include a bus 610, a processor 620, a memory 630, a storage component 640, an input component 650, an output component 660, and a communication component 670.

Bus 610 includes a component that enables wired and/or wireless communication among the components of device 600. Processor 620 includes a central processing unit, a graphics processing unit, a microprocessor, a controller, a microcontroller, a digital signal processor, a field-programmable gate array, an application-specific integrated circuit, and/or another type of processing component. Processor 620 is implemented in hardware, firmware, or a combination of hardware and software. In some implementations, processor 620 includes one or more processors capable of being programmed to perform a function. Memory 630 includes a random access memory, a read only memory, and/or another type of memory (e.g., a flash memory, a magnetic memory, and/or an optical memory).

Storage component 640 stores information and/or software related to the operation of device 600. For example, storage component 640 may include a hard disk drive, a magnetic disk drive, an optical disk drive, a solid state disk drive, a compact disc, a digital versatile disc, and/or another type of non-transitory computer-readable medium. Input component 650 enables device 600 to receive input, such as user input and/or sensed inputs. For example, input component 650 may include a touch screen, a keyboard, a keypad, a mouse, a button, a microphone, a switch, a sensor, a global positioning system component, an accelerometer, a gyroscope, and/or an actuator. Output component 660 enables device 600 to provide output, such as via a display, a speaker, and/or one or more light-emitting diodes. Communication component 670 enables device 600 to communicate with other devices, such as via a wired connection and/or a wireless connection. For example, communication component 670 may include a receiver, a transmitter, a transceiver, a modem, a network interface card, and/or an antenna.

Device 600 may perform one or more processes described herein. For example, a non-transitory computer-readable medium (e.g., memory 630 and/or storage component 640) may store a set of instructions (e.g., one or more instructions, code, software code, and/or program code) for execution by processor 620. Processor 620 may execute the set of instructions to perform one or more processes described herein. In some implementations, execution of the set of instructions, by one or more processors 620, causes the one or more processors 620 and/or the device 600 to perform one or more processes described herein. In some implementations, hardwired circuitry may be used instead of or in combination with the instructions to perform one or more processes described herein. Thus, implementations described herein are not limited to any specific combination of hardware circuitry and software.

The number and arrangement of components shown in FIG. 6 are provided as an example. Device 600 may include additional components, fewer components, different components, or differently arranged components than those shown in FIG. 6. Additionally, or alternatively, a set of components (e.g., one or more components) of device 600 may perform one or more functions described as being performed by another set of components of device 600.

Figure 7:
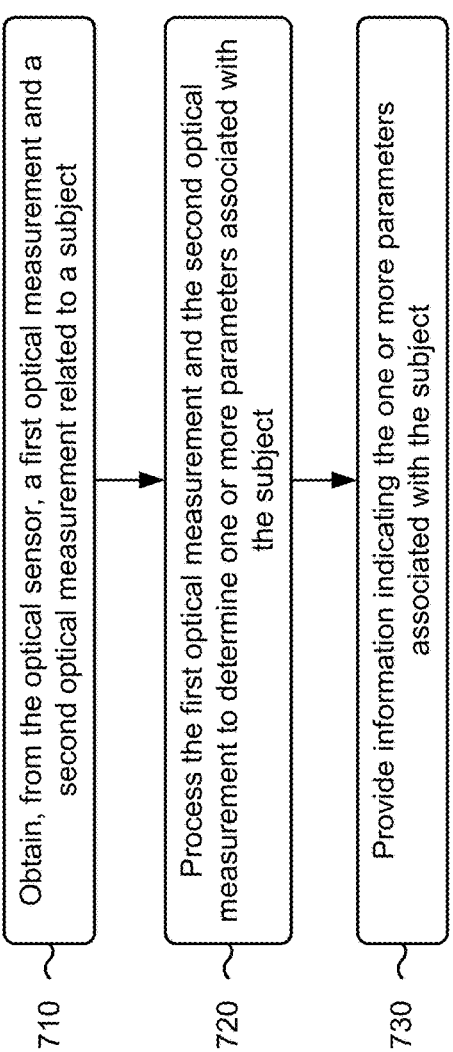
FIG. 7 is a flowchart of an example process associated with an optical sensor device described herein.

FIG. 7 is a flowchart of an example process 700 associated with an optical sensor device (e.g., optical sensor device 102 and/or optical sensor device 510). In some implementations, one or more process blocks of FIG. 7 may be performed by one or more processors (e.g., one or more processors 138 and/or one or more processors 520) of the optical sensor device. In some implementations, one or more process blocks of FIG. 7 may be performed by another device or a group of devices separate from or including the one or more processors, such as an optical sensor (e.g., optical sensor 116 and/or optical sensor 530) of the optical sensor device, one or more other components of the optical sensor device 102, and/or a user device (e.g., user device

540). Additionally, or alternatively, one or more process blocks of FIG. 7 may be performed by one or more components of device 600, such as processor 620, memory 630, storage component 640, input component 650, output component 660, and/or communication component 670.

As shown in FIG. 7, process 700 may include obtaining, from the optical sensor, a first optical measurement and a second optical measurement related to a subject (block 710). For example, the one or more processors may obtain, from the optical sensor, a first optical measurement and a second optical measurement related to a subject, as described above. In some implementations, the first optical measurement indicates an amount of light associated with a particular wavelength range that the sensor element accumulated during a first time range, and the second optical measurement indicates an amount of light associated with the particular wavelength range that the sensor element accumulated during a second time range, wherein the first time range is a subrange of the second time range.

As further shown in FIG. 7, process 700 may include processing the first optical measurement and the second optical measurement to determine one or more parameters associated with the subject (block 720). For example, the one or more processors may process the first optical measurement and the second optical measurement to determine one or more parameters associated with the subject, as described above.

As further shown in FIG. 7, process 700 may include providing information indicating the one or more parameters associated with the subject (block 730). For example, the one or more processors may provide information indicating the one or more parameters associated with the subject, as described above.

Process 700 may include additional implementations, such as any single implementation or any combination of implementations described below and/or in connection with one or more other processes described elsewhere herein.

In a first implementation, a difference between an ending time of the first time range and an ending time of the second time range is less than 10 nanoseconds.

In a second implementation, alone or in combination with the first implementation, the subject comprises multiple layers and processing the first optical measurement and the second optical measurement to determine the one or more parameters associated with the subject includes determining, based on the particular wavelength range and the first time range, that the first optical measurement is related to a first layer of the subject; processing, based on determining that the first optical measurement is related to the first layer of the subject, the first optical measurement to determine one or more first characteristics associated with the first layer; determining, based on the particular wavelength range and the second time range, that the second optical measurement is related to at least a second layer of the subject; processing, based on determining that the second optical measurement is related to at least the second layer of the subject, the first optical measurement and the second optical measurement to determine one or more second characteristics associated with the second layer; and processing the one or more first characteristics and the one or more second characteristics to determine the one or more parameters associated with the subject.

In a third implementation, alone or in combination with one or more of the first and second implementations, processing the first optical measurement and the second optical measurement to determine the one or more second characteristics associated with the second layer includes determining a difference between the first optical measurement and the second optical measurement and processing the difference to determine the one or more second characteristics associated with the second layer.

In a fourth implementation, alone or in combination with one or more of the first through third implementations, the subject comprises multi-layered tissue of a human body, and the one or more parameters associated with the subject comprise one or more health parameters associated with the human body.

In a fifth implementation, alone or in combination with one or more of the first through fourth implementations, the one or more health parameters comprise at least one of a cardiac output parameter, a respiration rate parameter, a vascular disease parameter, an arterial compliance parameter, an endothelial function parameter, a venous condition assessment parameter, a vasospastic condition parameter, a microvascular flow parameter, a tissue viability parameter, an autonomic function parameter, a vasomotor function parameter, a thermoregulation parameter, an orthostasis parameter, a vasoconstriction parameter, a body fat composition parameter, a food sensitivity response parameter, a pharmaceutical sensitivity response parameter, a skin coloring or tanning response parameter, an electrolyte level parameter, a carbon monoxide level parameter, a hydration level parameter, a blood glucose level parameter, a blood pressure parameter, a blood oxygen parameter, or a heart rate parameter.

In a sixth implementation, alone or in combination with one or more of the first through fifth implementations, providing the information indicating the one or more parameters associated with the subject includes causing display of the information indicating the one or more parameters associated with the subject on a display screen associated with the optical sensor device.

In a seventh implementation, alone or in combination with one or more of the first through sixth implementations, processing the first optical measurement and the second optical measurement to determine the one or more parameters associated with the subject includes determining, based on the particular wavelength range and the first time range, that the first optical measurement is related to a first depth range of the subject; processing, based on determining that the first optical measurement is related to the first depth range of the subject, the first optical measurement to determine one or more first characteristics associated with the first depth range; determining, based on the particular wavelength range and the second time range, that the second optical measurement is related to at least a second depth range of the subject; processing, based on determining that the second optical measurement is related to at least the second depth range of the subject, the first optical measurement and the second optical measurement to determine one or more second characteristics associated with the second depth range; and processing the one or more first characteristics and the one or more second characteristics to determine the one or more parameters associated with the subject.

In an eighth implementation, alone or in combination with one or more of the first through seventh implementations, the one or more first characteristics comprise at least one of an absorption characteristic related to light that is associated with the first wavelength range, or a scatter characteristic related to light that is associated with the first wavelength range.

In a ninth implementation, alone or in combination with one or more of the first through eighth implementations, the subject comprises mammalian tissue and the one or more parameters associated with subject comprise one or more health parameters associated with the mammalian tissue.

In a tenth implementation, alone or in combination with one or more of the first through ninth implementations, the one or more health parameters comprise a blood glucose level parameter.

Although FIG. 7 shows example blocks of process 700, in some implementations, process 700 may include additional blocks, fewer blocks, different blocks, or differently arranged blocks than those depicted in FIG. 7. Additionally, or alternatively, two or more of the blocks of process 700 may be performed in parallel.

The foregoing disclosure provides illustration and description, but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein.

As used herein, satisfying a threshold may, depending on the context, refer to a value being greater than the threshold, greater than or equal to the threshold, less than the threshold, less than or equal to the threshold, equal to the threshold, not equal to the threshold, or the like.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set. As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiple of the same item.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, or a combination of related and unrelated items), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. An optical sensor device, comprising:
an optical sensor comprising an array of sensor elements and configured to provide optical measurements, related to light associated with a particular wavelength range that has propagated through a multi-layered subject, at time intervals of less than 10 nanoseconds;
an optical filter disposed over the optical sensor,
wherein the optical filter is configured to pass the light associated with the particular wavelength range to a sensor element of the array; and
one or more processors configured to:
obtain, from the optical sensor and at the time intervals of less than 10 nanoseconds, the optical measurements,
wherein the optical measurements include a first optical measurement and a second optical measurement,
wherein the first optical measurement indicates a first amount of the light associated with the particular wavelength range that the sensor element accumulated during a first time range, and
wherein the second optical measurement indicates a second amount of the light associated with the particular wavelength range that the sensor element accumulated during a second time range,
wherein the first time range is a subrange of the second time range;
process the first optical measurement to determine one or more first characteristics associated with a first layer of the multi-layered subject;
process a difference between the first optical measurement and the second optical measurement to determine one or more second characteristics associated with a second layer of the multi-layered subject; and
provide, based on the one or more first characteristics and the one or more second characteristics, information indicating one or more parameters associated with the multi-layered subject.

2. The optical sensor device of claim 1, wherein a difference between an ending time of the first time range and an ending time of the second time range is less than 10 nanoseconds.

3. The optical sensor device of claim 1, wherein the optical sensor comprises:
a photodiode configured to capture the light associated with the particular wavelength range and generate a photocurrent;
a storage diode configured to accumulate a charge associated with the photocurrent generated by the photodiode;
one or more gates configured to transfer the accumulated charge from the storage diode to a converter,
wherein the one or more gates are configured to transfer the accumulated charge based on a transfer cycle with a period that is less than 10 nanoseconds; and
the converter, wherein the converter is configured to convert the accumulated charge to an optical measurement.

4. The optical sensor device of claim 1, wherein the multi-layered subject comprises multi-layered tissue of a human body, and wherein the one or more parameters associated with multi-layered subject comprise one or more health parameters associated with the human body.

5. The optical sensor device of claim 1, wherein, to provide the information indicating the one or more parameters, the one or more processors are configured to:
provide, based on the one or more first characteristics and the one or more second characteristics, information indicating five or more of:
a cardiac output parameter;
a respiration rate parameter;
a vascular disease parameter;
an arterial compliance parameter;
an endothelial function parameter;
a venous condition assessment parameter;
a vasospastic condition parameter;
a microvascular flow parameter;
a tissue viability parameter;
an autonomic function parameter;
a vasomotor function parameter;
a thermoregulation parameter;
an orthostasis parameter;
a vasoconstriction parameter;
a body fat composition parameter;
a food sensitivity response parameter;
a pharmaceutical sensitivity response parameter;
a skin coloring or tanning response parameter;
an electrolyte level parameter;
a carbon monoxide level parameter;
a hydration level parameter;
a blood glucose level parameter;
a blood pressure parameter;
a blood oxygen parameter; or
a heart rate parameter.

6. The optical sensor device of claim 1, wherein the one or more processors, when providing the information indicating the one or more parameters associated with the multi-layered subject, are configured to:
cause display of the information indicating the one or more parameters associated with the multi-layered subject on a display screen associated with the optical sensor device.

7. The optical sensor device of claim 1, wherein the optical filter includes an optical channel that is disposed over the sensor element and is configured to prevent light associated with at least one other wavelength range from passing to the sensor element.

8. A method, comprising:
providing, by an optical sensor of an optical sensor device comprising an array of sensor elements, optical measurements, related to light associated with a particular wavelength range that has propagated through a multi-layered subject, at time intervals of less than 10 nanoseconds, wherein an optical filter is disposed over the optical sensor and is configured to pass the light associated with the particular wavelength range to the array of sensor elements;
processing, by the optical sensor device, a first optical measurement of the optical measurements to determine one or more first characteristics associated with a first layer of the multi-layered subject,
wherein the first optical measurement indicates a first amount of the light associated with the particular wavelength range and accumulated during a first time range;
processing, by the optical sensor device, a second optical measurement of the optical measurements to determine one or more second characteristics associated with a second layer of the multi-layered subject,
wherein the second optical measurement indicates a second amount of the light associated with the particular wavelength range and accumulated during a second time range, and
wherein the first time range is a subrange of the second time range; and
providing, by the optical sensor device and based on the one or more first characteristics and the one or more second characteristics, information indicating one or more parameters associated with the multi-layered subject.

9. The method of claim 8, wherein a difference between an ending time of the first time range and an ending time of the second time range is less than 10 nanoseconds.

10. The method of claim 8, further comprising:
generating, using a photodiode of the optical sensor device, a photocurrent by capturing the light associated with the particular wavelength range;
accumulating, using a storage diode of the optical sensor device, a charge associated with the photocurrent;
transferring, based on a transfer cycle with a period that is less than 10 nanoseconds, the accumulated charge from the storage diode to a converter; and
converting the accumulated charge to the first optical measurement.

11. The method of claim 8, wherein the multi-layered subject comprises multi-layered tissue of a human body, and
wherein the one or more parameters comprise one or more health parameters associated with the human body.

12. The method of claim 11, wherein the one or more health parameters comprise at least one of:
a cardiac output parameter;
a respiration rate parameter;
a vascular disease parameter;
an arterial compliance parameter;
an endothelial function parameter;
a venous condition assessment parameter;
a vasospastic condition parameter;
a microvascular flow parameter;
a tissue viability parameter;
an autonomic function parameter;
a vasomotor function parameter;
a thermoregulation parameter;
an orthostasis parameter;
a vasoconstriction parameter;
a body fat composition parameter;
a food sensitivity response parameter;
a pharmaceutical sensitivity response parameter;
a skin coloring or tanning response parameter;
an electrolyte level parameter;
a carbon monoxide level parameter;
a hydration level parameter;
a blood glucose level parameter;
a blood pressure parameter;
a blood oxygen parameter; or
a heart rate parameter.

13. The method of claim 8, wherein providing the information indicating the one or more parameters comprises:
causing display of the information indicating the one or more parameters on a display screen associated with the optical sensor device.

14. The method of claim 8, further comprising:
passing the light associated with the particular wavelength range to a sensor element of the array of sensor elements while preventing light associated with at least one other wavelength range from passing to the sensor element.

15. An apparatus, comprising:
means for obtaining, from an optical sensor comprising an array of sensor elements, optical measurements, related to light associated with a particular wavelength range that has propagated through a multi-layered subject, at time intervals of less than 10 nanoseconds, wherein an optical filter is disposed over the optical sensor and is configured to pass the light associated with the particular wavelength range to the array of sensor elements;
means for processing a first optical measurement of the optical measurements to determine one or more first characteristics associated with a first layer of the multi-layered subject,
wherein the first optical measurement indicates a first amount of the light associated with the particular wavelength range and accumulated during a first time range;
means for processing a second optical measurement of the optical measurements to determine one or more second characteristics associated with a second layer of the multi-layered subject,
wherein the second optical measurement indicates a second amount of the light associated with the particular wavelength range and accumulated during a second time range, and
wherein the first time range is a subrange of the second time range; and
means for providing, based on the one or more first characteristics and the one or more second characteristics, information indicating one or more parameters associated with the multi-layered subject.

16. The optical sensor device of claim 3, wherein the optical sensor further comprises:
a modulation gate configured to transfer the photocurrent to the storage diode.

17. The optical sensor device of claim 3, wherein the optical sensor further comprises:
a floating diffusion configured to provide the accumulated charge to the converter.

18. The optical sensor device of claim 17, wherein the optical sensor further comprises:
a transfer gate configured to transfer the accumulated charge to the floating diffusion.

19. The optical sensor device of claim 17, wherein the optical sensor further comprises:
a charge-transfer assisting gate configured to transfer the accumulated charge to the floating diffusion.

20. The optical sensor device of claim 1, wherein the optical measurements include an initial optical measurement; and
wherein the one or more processors are configured to:
modify the first optical measurement based on the initial optical measurement before processing the first optical measurement.

* * * * *